United States Patent
Schmidt et al.

(10) Patent No.: US 7,127,146 B2
(45) Date of Patent: Oct. 24, 2006

(54) APPARATUS FOR OPTICAL MEASUREMENTS ON LOW-INDEX NON-SOLID MATERIALS BASED ON ARROW WAVEGUIDES

(75) Inventors: Holger Schmidt, Capitola, CA (US); Aaron Roe Hawkins, Provo, UT (US)

(73) Assignees: The Regents of the University of California, Oakland, CA (US); Brigham Young University, Provo, UT (US)

( * ) Notice: Subject to any disclaimer, the term of this patent is extended or adjusted under 35 U.S.C. 154(b) by 9 days.

(21) Appl. No.: 11/223,293

(22) Filed: Sep. 9, 2005

(65) Prior Publication Data

US 2006/0008227 A1    Jan. 12, 2006

Related U.S. Application Data

(63) Continuation of application No. 10/868,475, filed on Jun. 15, 2004.

(60) Provisional application No. 60/479,376, filed on Jun. 16, 2003.

(51) Int. Cl.
*G02B 6/10* (2006.01)
(52) U.S. Cl. ........................................ 385/129; 385/12
(58) Field of Classification Search ................. 385/12, 385/129–133, 141–143
See application file for complete search history.

(56) References Cited

U.S. PATENT DOCUMENTS

| | | | |
|---|---|---|---|
| 5,184,192 A | 2/1993 | Gilby et al. | 356/246 |
| 5,416,879 A | 5/1995 | Liu | 385/125 |
| 5,444,807 A | 8/1995 | Liu | 385/125 |
| 5,561,523 A | 10/1996 | Blomberg et al. | 356/454 |
| 5,920,391 A | 7/1999 | Grasdepot et al. | 356/519 |
| 6,137,108 A | 10/2000 | DeThomas et al. | 250/339.07 |
| 6,199,257 B1 | 3/2001 | Munk et al. | 29/423 |
| 6,332,049 B1 | 12/2001 | Dasgupta | 385/12 |
| 6,542,231 B1 | 4/2003 | Garrett | 356/246 |
| 6,600,558 B1* | 7/2003 | Ueno et al. | 356/246 |
| 6,784,988 B1 | 8/2004 | Vijayakumar et al. | 356/244 |
| 6,839,140 B1 | 1/2005 | O'Keefe et al. | 356/436 |
| 6,867,857 B1 | 3/2005 | Hobbs | 356/246 |
| 6,870,626 B1 | 3/2005 | Autrey et al. | 356/432 |

OTHER PUBLICATIONS

Archambault, J-L, et al., "Loss calculations for antiresonant waveguides," *J. Lightwave Technol.*, 1993, 11(3), 416-423.

(Continued)

*Primary Examiner*—Kevin S. Wood
(74) *Attorney, Agent, or Firm*—Woodcock Washburn LLP

(57) ABSTRACT

An optical waveguide is constructed so as to comprise a non-solid core layer surrounded by a solid-state material. The non-solid core layer has an index of refraction which is lower than the index of refraction of the surrounding solid-state material, and light can be transmitted with low loss through the non-solid core layer. In an exemplary application, the non-solid core layer comprises a sample material whose light transmission, absorption, and/or interference characteristics are to be measured. In addition, a perpendicular waveguide portion may be included for use in injecting light into the core for measuring fluorescence characteristics associated with the sample material. Most preferably, the optical waveguide is generally structured as an anti-resonant reflecting optical waveguide (ARROW), which comprises a Fabry-Perot reflector adjacent to the core layer, whereby light is substantially prevented from leaking out of said core in a transverse direction.

35 Claims, 11 Drawing Sheets
(9 of 11 Drawing Sheet(s) Filed in Color)

OTHER PUBLICATIONS

Armenise, M. et al., "Modeling and design of a novel miniaturized integrated optical sensor for gyroscope systems," *J. Lightwave Technol.*, 2001, 19(10), 1476-1494.

Ashkin, A., "History of optical trapping and manipulation of small-neutral particle, atoms, and molecules," *IEEE Journal of Selected Topics in Quantum Electronics*, Nov.-Dec., 2000, 6(6), 841-856.

Bartenstein, M. et al., "Atoms and Wires: Toward Atom Chips," *IEEE Journal of Quantum Electronics*, 2000, 36(12), 1364-1377.

Benaissa, K. et al., "IC compatible optical coupling techniques for integration of ARROW with photodetector," *J. Lightwave Technology*, 1998, 16(8), 1423-1432.

Bernini, R. et al. "Silicon Micromachined Hollow Optical Waveguides for Sensing Applications", *IEEE J. Sel. Top. Quant. Elec.*, 2002, 8(1), 106-110.

Cantin, M. et al., "Remotely switched hollow-core antiresonant reflecting optical waveguide," *Opt. Lett.*, 1991, 16(22), 1738-1740.

Castro, A. et al., "Single-Molecule detection of specific nucleic acid sequences in unamplified genomic DNA," *Anal. Chem.*, 1997, 69, 3915-3920.

Chow, W.W. et al., "The ring laser gyro," *Rev. Mod. Phys.*, 1985, 57(1), 61 -104.

Coldren, L.A. et al., *Diode Lasers and Photonic Integrated Circuits*, Wiley & Sons, Inc., 1995, Appendix 3, 428-440.

Datta A. et al. "Microfabrication and characterization of teflon AF-coated liquid core waveguide channels in silicon," *IEEE Sensors J.*, Dec. 2003, 3(6). 788-795.

Duguay, M.A., et al., "Antiresonant reflecting optical waveguides in $SiO_2$-Si multilayer structures," *Appl. Phys. Lett.*, 1986, 49(1), 13-15.

Fano, U., "Effects of Configuration Interaction on Intensities and Phase Shifts," *Phys. Rev.*, 1961, 124(6), 1866-1878.

Fill, E.E. et al., "Lasing without inversion via the lambda quantum-beat laser in the collision-dominated regime," *Opt. Comm.*, 1990, 77(1), 36-40.

Fink, Y. et al., "A dielectric omnidirectional reflector," *Science*, 1998, 282, 1679-1682.

Gifford, S.C. et al., "Parallel microchannel-based measurements of individual erythrocyte areas and volumes," *Biophysical J.*, 2003, 84, 623-633.

Gray, H.R. et al., "Coherent trapping of atomic populations," *Opt. Lett.*, 1978, 3(6), 218-220.

Gustavson, T.L. et al., "Precision Rotation measurements with an atom interferometer gyroscope," *Phys. Rev. Lett.*, 1997, 78(11), 2046-2049.

Gustavson, T.L. et al., "Rotation sensing with a dual atom-interferometer Sagnac gyroscope," *Class. Quantum Grav.*, 2000, 17, 2385-2398.

Hänsel, W. et al., "Bose-Einstein condensation on a microelectronic chip," *Nature*, 2001, 413, 498-501.

Harris, S.E. et al., "Nonlinear optical processes using electromagnetically induced transparency," *Phys. Rev. Lett.*, 1990, 64(10), 1107-1110.

Harris, S.E., "Lasers without inversion: interference of lifetime-broadened resonances," *Phys. Rev. Lett.*, 1989, 62(9), 1033-1036.

Imamoglu, A. et al., "Strongly interacting photons in a nonlinear cavity," *Phys. Rev. Lett.*, 1997, 79(8), 1467-1470.

Ivnitski, D. et al., "Biosensors for detection of pathogenic bacteria," *Biosensors & Bioelectronics.*, 1999, 14, 599-624.

Kasapi, A. et al., "Electromagnetically induced transparency: propagation dynamics," *Phys. Rev. Lett.*, 1995, 74(13), 2447-2451.

Kitching, J. et al., "Miniature vapor-cell atomic frequency references," *Appl. Phys. Lett.*, 2002, 81(3), 553-555.

Koch, T.L. et al., "Antiresonant reflecting optical waveguides for III-V integrated optics," *Elec. Lett.*, 1987, 23, 244-245.

Kranz, M. et al., "A single-layer Silicon-on-Insulator MEMS gyroscope for wide dynamic range and harsh environment applications," *Proc. of the SPIE.*, 2001, 4459, 5-8.

Leistiko O. et al., "Integrated bio/chemical microsystems employing optical detection: the clip-on," *J. Micromech. Microeng.*, 1998, 8(2), 148-50.

Levene, M.J. et al., "Zero-mode waveguides for single-molecule analysis at high concentrations," *Science*, 2003, 299, 682-686.

Lim, H. et al., "A few deg/hr resolvable low noise lateral microgyroscope," *Technical Digest, MEMS 2002 IEEE International Conference*, 2002, 627.

Lin, S. et al., "Sensitivity analysis of the Sagnac-effect optical-fiber ring interferometer," *Applied Optics.*, 1979, 18(6), 915-931.

LIttle, B.E. et al., "Ultra-compact Si-$SiO_2$ microring resonator optical channel dropping filters," *IEEE Photonics Technology Letters*, 1998, 10(4), 549-551.

Liu, B. et al., "Wide tunable double ring resonator coupled lasers," *IEEE Photonics Technology Letters*, 2002, 14(5), 600-602.

Lou, H.J. et al., "Femtoliter microarray wells for ultrasensitive DNA/mRNA detection," *Instrumentation Science & Technology*, 2002, 30(4), 465-476.

Lukin, M.D. et al., "Intracavity electromagnetically induced transparency," *Opt. Lett.*, 1998, 23(4), 295-297.

Maltsev, V.P., "Scanning flow cytometry for individual particle analysis," *Review of Scientific Instruments*, 2000, 71(1), 243-255.

Mawst, L.J. et al., "Design optimization of ARROW-type diode lasers," *IEEE Photonics Technology Letters*, 1992, 4(11), 1204-1206.

Medina, M. et al., "Fluorescence correlation spectroscopy for the detection and study of single molecules in biology," *BioEssays*, 2002, 24, 758-764.

Miura, T. et al., "Novel phase-tunable three-dimensional hollow waveguides with variable air core," *IEEE Photonics Technology Letters*, 2003, 15(9), 1240-1242.

Miyagi, M. et al., "A proposal for low-loss leaky waveguide for submillimeter waves transmission," *IEEE Trans. on Microwave Theory and Tech.*, 1980, MTT-28(4), 398-401.

Nathan, A. et al., "Silicon integrated optic devices and micromechanical sensors based on ARROW," *Proceedings*: SPIE—*The International Society for Optical Engineering*, San Jose, California, Jan. 29, 1996, 2686, 2-16.

Padmabandu, G.G. et al., "Laser oscillation without population inversion in a sodium atomic beam," *Phys. Rev. Lett.*, 1996, 76(12), 2053-2056.

Paternostro, M. et al., "Generation of entangled coherent states via cross-phase-modulation in a double electromagnetically induced transparency regime," *Phys. Rev. A*, 2003, 67, 023811-1 thru 023811-15.

Patterson, S.G. et al., "Continuous-wave room temperature operation of bipolar cascade laser," *Electronics Letters.*, 1999, 35(5), 395-397.

Resch, K.J. et al., "Electromagnetically induced opacity for photon pairs," *Journal of Modern Optics*, 2002, 49(3/4), 487-502.

Rostovtsev, Y. et al., "Slow, ultraslow, stored, and frozen light," *Optics & Photonics News.*, 2002, 13, 44-48.

Rowe, C.H. et al., "Design and operation of a very large ring laser gyroscope," *Applied Optics*, 1999, 38(12), 2516-2523.

Russell, P., "Holey fiber concept spawns optical-fiber renaissance," *Laser Focus World*, 2002, 38, 77-82.

Saito, Y. et al., "Experimental trial of a hollow-core waveguide used as an absorption cell for concentration measurement of $NH_3$ gas with a $CO_2$ laster," *Opt. Lett.*, 1993, 18(24), 2150-2152.

Schmidt, H. et al., "Integrated optical spectroscopy of low-index gases and liquids using ARROW waveguides," *Integrated Photonics Research Conference*, 2003, 3 pages.

Schmidt, H. et al., "Giant Kerr nonlinearities using electromagnetically induced transparency," *Optics Letters*, 1996, 21(23), 1936-1938.

Schmidt, H. et al., "High-speed properties of a phase-modulation scheme baesd on electromagnetically induced transparency," *Optics Letters*, 1998, 23(13), 1007-1009.

Scully, M.O. et al., "High-sensitivity magnetometer based on index-enhanced media," *Phy. Rev. Lett.*, 1992, 69(9), 1360-1363.

Scully, M.O. et al., "Field-field and photon-photon interferometry," *Quantum Optics*, 1997, Chapter 4.1, 97-111.

Suzuki, K. et al., "Monolithically integrated resonator microoptic gyro on silica planar lightwave circuit," *J. of Lightwave Technology*, 2000, 18(1), 66-72.

Temelkuran, B. et al., "Wavelength-scalable hollow optical fibres with large photonic bandgaps for $CO_2$ laser transmission," *Nature*, 2002, 420, 650-653.

Wang, S-L. et al., "A Miniaturized Liquid Core Waveguide-Capillary Electrophoresis System with Flow Injection Sample Introduction and Fluorometric Detection Using Light-Emitting Diodes," *Anal. Chem.*, 2001, 73, 4545-4549.

Webb, W.W., "Fluorescence correlation spectroscopy: inception, biophysical experimentations, and prospectus," *Applied Optics*, 2001, 40(24), 3969-3983.

Woolley, A.T. et al., "Direct haplotyping of kilobase-size DNA using carbon nanotube probes," *Nature Biotechnology*, 2000, 18, 760-763.

Campopiano et al., "Microfluidic sensor based on integrated optical hollow waveguides," *Optics Letters*, 2004, 29(16), 1894-1896.

Delonge, T. et al., "Integrated optical detection cell based on Bragg reflecting waveguides," *Journal of Chromatography A*, 1995, 716, 135-139.

\* cited by examiner

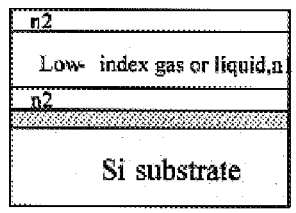
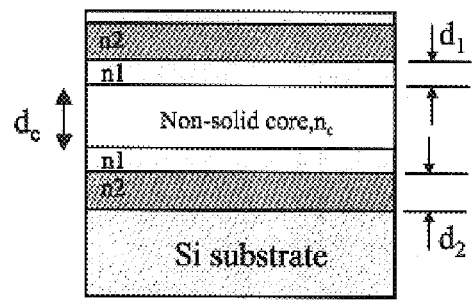
FIGURE 6(a)   FIGURE 6(b)
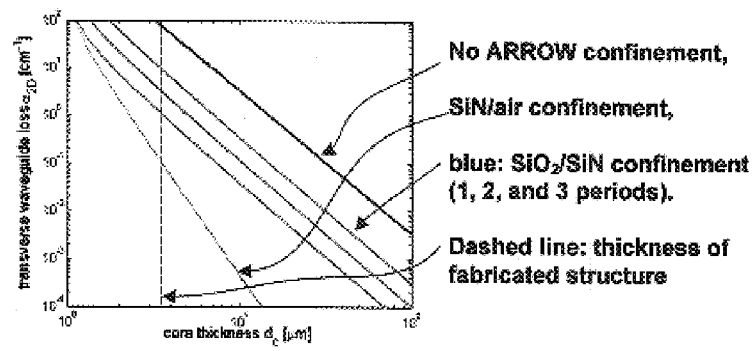
FIGURE 6(c)
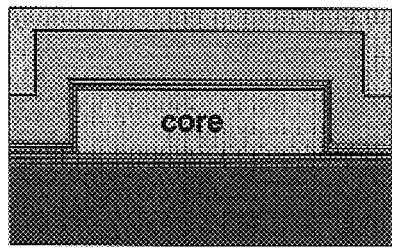
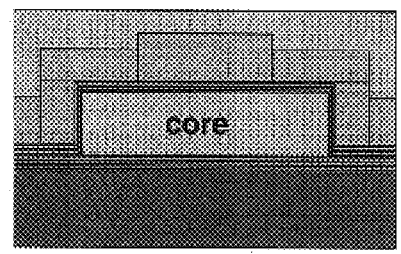
FIGURE 6(d)   FIGURE 6(e)
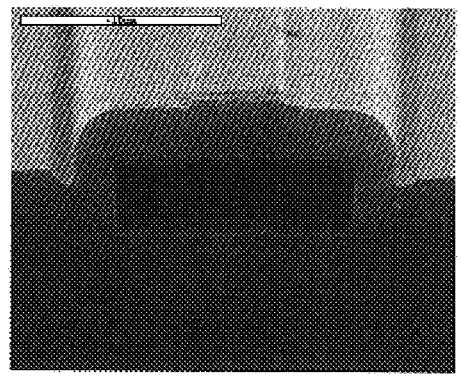
FIGURE 6(f)

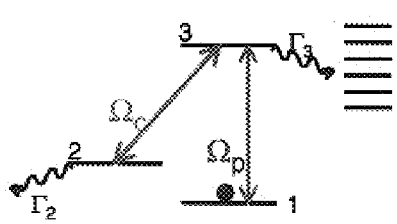
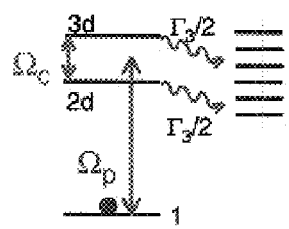
FIGURE 12(a)　　　　　FIGURE 12(b)
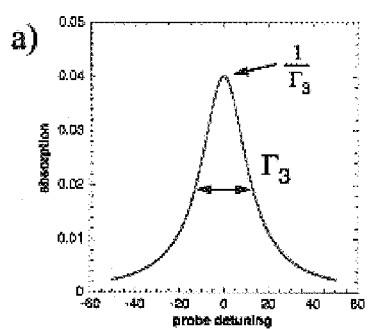
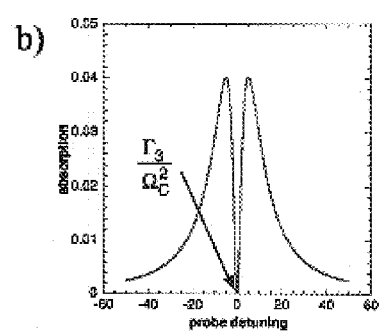
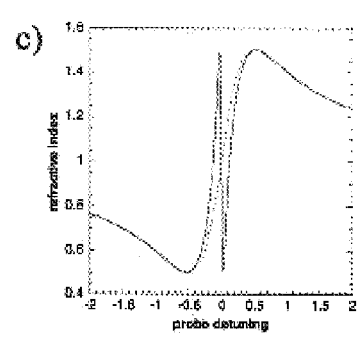
FIGURE 13(a)　　　FIGURE 13(b)　　　FIGURE 13(c)

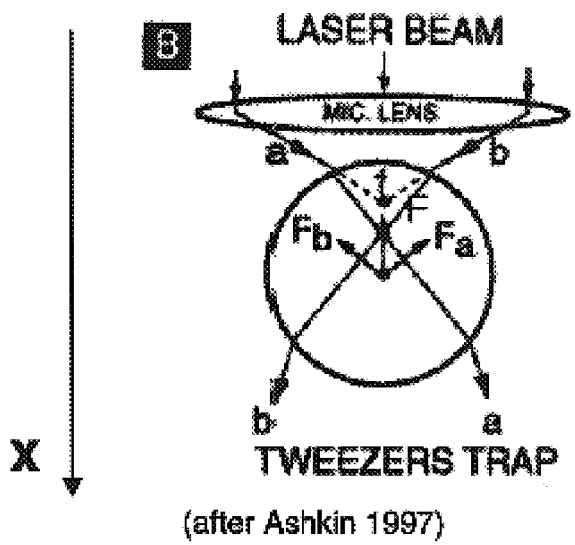
FIGURE 16(a) (PRIOR ART)
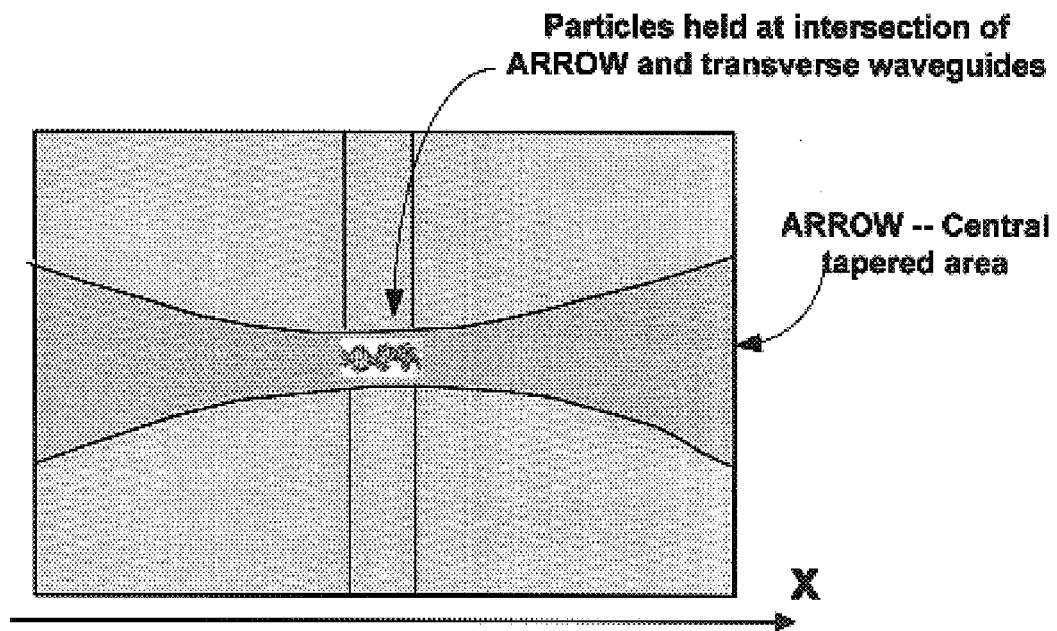
FIGURE 16(b) (TOP VIEW OF ARROW WAVEGUIDE)

APPARATUS FOR OPTICAL MEASUREMENTS ON LOW-INDEX NON-SOLID MATERIALS BASED ON ARROW WAVEGUIDES

CROSS REFERENCE

This application is a continuation of U.S. patent application Ser. No. 10/868,475, filed Jun. 15, 2004, now pending, which is hereby incorporated by reference in its entirety. This application also claims the benefit of U.S. Provisional Application No. 60/479,376, filed Jun. 16, 2003.

TECHNICAL FIELD

The present invention relates generally to the field of integrated optics, and more particularly to an optical waveguide comprising a non-solid core layer surrounded by a solid-state material, wherein light can be transmitted with low loss through the non-solid core layer. A presently preferred implementation of the invention employs antiresonant reflecting optical waveguides, known as ARROWs or ARROW waveguides.

BACKGROUND

Our invention provides a practical way to extend the field of integrated optics to non-solid waveguide core materials. That is, we describe a way for guiding light on a chip through non-solid materials such as gases and liquids. Light can not only interact with these materials at the location of the active elements in the integrated device, the connections ("optical wires") between elements can also occur through the non-solid materials. Before we explain certain background information relevant to our invention, it should be noted that, although we focus much attention to biomedical applications, the present invention is not limited to any specific application, biomedical or otherwise. The present invention may be applied to a broad range of problems, including but not limited to: the sensing of gases and liquids; single molecule spectroscopy (e.g., fluorescence); quantum optics and quantum information processing; optical measurements of extremely small volumes of gases and liquids; optical tweezers for manipulating tiny (microscopic) particles using light forces; implantable biomedical sensors, etc. Accordingly, except as they may be expressly so limited, the scope of protection of the claims at the end of this specification is by no means limited to the specific applications described herein.

Currently, there are a number of optical methods being used to improve human health and answer health-related scientific questions. These include both applications which are already well advanced (cell flow cytometry (Maltsev, V. P., "Scanning flow cytometry for individual particle analysis," *Rev. Sci. Inst.* 71, 243 (2000); Ivnitski, D. et al., "Biosensors for detection of pathogenic bacteria," *Biosensors and Bioelectronics* 14, 599 (1999)), blood measurements (Gifford, S. C. et al., "Parallel microchannel-based measurements of individual erythrocyte areas and volumes," *Biophysical Journal* 84, 623 (2003)) as well as very fundamental questions regarding the human body (e.g., basic understanding and counting of single DNA molecules. Levene, M. J. et al., "Zero-mode waveguides for single-molecule analysis at high concentrations," *Science* 299, 682 (2003)). Such single molecule studies are carried out to improve drug screening, mRNA expression profiling, and DNA sequencing. Castro, A., et al., "Single-Molecule detection of specific nucleic acid sequences in unamplified genomic DNA," *Anal. Chem.,* 69, 3915, (1997); Woolley, A. T. et al., "Direct haplotyping of kilobase-size DNA using carbon nanotube probes," *Nature Biotechnology* 18 760 (2000)). At the same time, there is a continuing trend to increase the sensitivity of biomedical sensors and imaging methods, down to very small sample volumes (Webb, W. W., "Fluorescence correlation spectroscopy: inception, biophysical experimentations, and prospectus," *Applied Optics* 24 3969 (2001); Lou, H. J. et al., "Femtoliter microarray wells for ultrasensitive DNA/mRNA detection," *Instrumentation Science and Technology* 30 465 (2002)) and individual molecules (DNA). Another area where exquisite sensitivity is required is detection of toxic substances in the gas phase (e.g., in air). We will describe below some specific examples of state-of-the-art methodologies that are currently being used, and describe their performance and limitations. Then we will describe our novel approach with emphasis on how existing problems are addressed and solved.

(i) DNA Fluorescence with Single Molecule Resolution

There are a couple of methods for optical measurements on single molecules. A popular one is to observe them using diffraction-limited optics (Medina, M. et al., "Fluorescence correlation spectroscopy for the detection and study of single molecules in biology," *Bioessays* 24, 758 (2002)). The principle of one technique—fluorescence correlation spectroscopy—is shown in FIG. 1(*a*). Problems associated with this method include the fact that only extremely small volumes on the order of fl are tolerable, and more importantly, that such setups are bulky in nature and cannot be scaled readily to multiple sample volumes.

A potentially significant improvement to some of these issues has recently been made by Levene et al. (Levene, M. J. et al., "Zero-mode waveguides for single-molecule analysis at high concentrations," *Science* 299, 682 (2003)), who developed a detection method with single molecule sensitivity based on evanescent coupling of light from molecules trapped in sub-micron sized holes in metal films. The principle is shown in FIG. 1(*b*) where enzymatic synthesis of double-stranded DNA by DNA polymerase using fluorescently tagged nucleotide analog coumarin-dCTP was measured.

Using such zero-mode waveguides, the observation volume can be increased to the micromolar level. However, while this method is clearly ingenious, it can be seen from FIG. 1(*b*) that the setup is still rather cumbersome and involves optical paths for excitation and detection that are perpendicular to the sample plane. The metal film contains a large number of these zero-mode waveguides, which results in large parallelism. However, since the fluorescence is collected through a microscope objective, a large number of these holes are interrogated simultaneously and deliberate readout from a single hole is impossible. In addition, evanescent waveguide coupling is a concept that is currently pursued by many groups to couple optical signals into waveguides. However, it is highly inefficient as it relies on detection of exponentially decaying electric field values of the fluorescence signal. As a result, no transport of the optical signal through a waveguide or all-optical post-processing is possible.

(ii) Flow Cytometry of Small Volumes

Another area in which optical interactions with a liquid sample containing biological material are being studied is flow cytometry. This field is rather well developed and an advanced setup capable of individual particle analysis (Maltsev, V. P., "Scanning flow cytometry for individual particle analysis," *Rev. Sci. Inst.* 71, 243 (2000)) is shown in FIG. 2(*a*).

In this case, a microchannel containing the specimen with a width of 10 μm is used. A laser is sent into this channel and fluorescence is detected perpendicular to the excitation direction. The important facts to note are that no waveguiding within the microcuvette is involved, measurements of multiple channels is impossible with this setup and the whole setup is composed of bulk optics.

Another example for a generic flow cytometry setup is shown in FIG. 2(*b*). In FIG. 2(*b*), a liquid sample containing potentially pathogenic bacteria is passed through a flow cell and the specimen is excited using a microscope objective in the perpendicular direction. This arrangement brings with it significant loss of the optical signal due to multiple interfaces between the sample space and the end of the microscope objective. In addition, only one channel can be excited this way as the focal depth of the excitation spot is very small and the excitation beam diverges quickly after it passes the flow cell. Leistiko et al. describe another realization of a microfluidic channel system for biological and biochemical applications Leistiko 0, Jensen P F. "Integrated bio/chemical microsystems employing optical detection: the clip-on." [Conference Paper] IOP Publishing. *Journal of Micromechanics & Microengineering*, vol. 8, no.2, June 1998, pp. 148–50. There, optical fibers are placed in etched grooves on a silicon substrate and covered with a pyrex slide. The light from the optical fibers is coupled into integrated waveguides in the silicon. However, they intersect an ordinary microcapillary which again leads to significant coupling losses into and out of the capillary leading to a coupling efficiency of only a few percent.

In light of the limitations and problems described above, and as discussed in greater detail below, we have invented a new approach to develop a planar integrated platform for such optical measurements with high sensitivity and the potential for massive parallelism. A presently preferred implementation of our invention is based on ARROW waveguides. (Miyagi, M. et al., "A proposal for low-loss leaky waveguide for submillimeter waves transmission," *IEEE Trans. On Microwave Theory and Tech.* 28, 298 (1980); Duguay, M. A., et al., "Antiresonant reflecting optical waveguides in $SiO_2$—Si multilayer structure," *Appl. Phys. Lett.* 49, 13 (1986)). We will first describe the principle behind these waveguides and then explain several ways in which they may be used.

In conventional waveguides, light is guided in a medium with higher refractive index than its surroundings (e.g., silica fiber/air). When the refractive index situation is reversed (e.g., in microcapillaries) light cannot be guided in the central low-index region (core) and will leak out as shown in FIG. 3(*a*). A solution to this problem is to prevent the transverse components of the propagation vector from leaking out. This can be accomplished by adding Fabry-Perot reflectors in the transverse direction as is shown in FIG. 3(*b*). The high-index layers will reflect most of the light propagating in the transverse direction (vertical direction in FIGS. 3(*a*), (*b*)). The thickness t of the high-index cladding layer is chosen correctly to yield the desired interference.

It is important to note that these structures are well-known in optoelectronics and photonics where they have mainly been used as design tools for high-power and cascade lasers (Mawst, L. J. et al., "Design optimization of ARROW-type diode lasers," *IEEE Phot. Technol. Lett.* 4, 1204 (1992); Patterson, S. G. et al., "Continuous-wave room temperature operation of bipolar cascade laser," *Electronics Letters* 35, 395 (1999)). In all applications, however, the ARROW waveguides were made using only solid-state semiconductor or dielectric materials. We are interested in ARROW waveguides where the low-index core is liquid or gaseous (Schmidt, H. et al., "Integrated optical spectroscopy of low-index gases and liquids using ARROW waveguides," *Integrated Photonics Research Conference*, Washington, D.C. (2003)). It should also be pointed out that light guiding in low-index media is also possible using photonic bandgap structures (Joannopoulus, J. D. et al., "Photonic crystals," Princeton University Press, 1995). However, such structures are extremely complicated to fabricate and cannot be used for some of the applications of interest here. They also rely on structures with long range periodicity which is not required for ARROW structures. In addition, fabrication of hollow core ARROW waveguides has been proposed using a different fabrication method (R. Bernini, S. Campopiano, and L. Zeni, "Silicon Micromachined Hollow Optical Waveguides for Sensing Applications", IEEE J. Sel. Top. Quant. Elec. 8, 106–110 (2002)). Finally, a method for index-guiding through aqueous liquids in large diameter (several 100 microns) Teflon waveguides was demonstrated (Datta A, In-Yong Eom, Dhar A, Kuban P, Manor R, Ahmad I, Gangopadhyay S, Dallas T, Holtz M, Temkin H, Dasgupta P K. "Microfabrication and characterization of Teflon AF-coated liquid core waveguide channels in silicon." [Journal Paper] *IEEE Sensors Journal, vol.* 3, no.6, December 2003, pp. 788–95). Single-mode propagation and light confinement in gases is not possible with this approach.

SUMMARY

In a presently preferred embodiment of the invention, an optical waveguide is constructed so as to comprise a non-solid core layer surrounded by a solid-state material. In particular, unlike the micromachined structure disclosed by Bernini, et al., in "Silicon Micromachined Hollow Optical Waveguides for Sensing Applications", supra, the optical waveguide includes a substrate and multiple layers of solid state material disposed on the substrate, and a non-solid core extending through at least one of the multiple layers. The substrate can be made of Silicon (Si) or other solid material. The waveguides in question could be made on different semiconductor substrates but also on a smooth metal, ceramic, or plastic surface. The non-solid core may be used to contain a sample material whose light transmission, absorption, and/or interference characteristics are to be measured. The sample may have an index of refraction which is lower than the index of refraction of the surrounding solid-state material, and light can be transmitted with low loss through the non-solid core layer and sample material.

In an exemplary application of the invention, a perpendicular waveguide portion may be included for use in injecting light into the core for measuring fluorescence characteristics associated with the sample material. Most preferably, the optical waveguide is generally structured as an anti-resonant reflecting optical waveguide (ARROW), which comprises a Fabry-Perot reflector adjacent to the core layer, whereby light is substantially prevented from leaking out of said core in a transverse direction.

The present invention may also be embodied in an optical measurement system comprising (a) an optical waveguide comprising a channel surrounded by a solid-state material, including a Fabry-Perot reflector adjacent to the channel, (b) means for injecting into the channel a sample material having an index of refraction which is lower than the index of refraction of the surrounding solid-state material; (c) means for injecting light into the channel, wherein the injected light is guided within the channel and through the sample material; (d) a perpendicular waveguide portion for use in injecting light into the channel; and (e) means for measuring selected optical properties associated with the sample.

In accordance with another aspect of the invention, a system for making parallel optical measurements is provided. An embodiment of the inventive system comprises: (a) an optical waveguide comprising a generally planar solid-state material and a plurality of parallel channels within the solid-state material, including a Fabry-Perot reflector adjacent to each channel, whereby light injected into the channels is substantially prevented from leaking out of said channels in a transverse direction; (b) means for injecting through each of the channels a sample material having an index of refraction which is lower than the index of refraction of the surrounding solid-state material; (c) a perpendicular waveguide portion for use in injecting light into the channels in a direction which is generally perpendicular to the orientation of the channels and the flow of sample materials; and (d) means for measuring selected optical properties associated with the sample materials.

In addition, the present invention may also be employed to provide device for realizing large nonlinear phase shifts between single photons based on the realization of electromagnetically induced transparency (EIT) in Rb atoms that are introduced in the optical waveguide.

In yet another embodiment, the present invention may be employed to provide optical tweezers for manipulating very small particles using light.

Other features and advantages of the present invention are described below.

BRIEF DESCRIPTION OF THE DRAWINGS

The file of this patent contains at least one drawing/photograph executed in color. Copies of this patent with color drawings/photographs will be provided by the Office upon request and payment of the necessary fee.

FIG. 6(a) depicts a single-ARROW structure in which only the first cladding layer (thickness t1) is antiresonant and provides guiding. FIG. 6(b) depicts a double-ARROW structure in which both the first and second cladding layers (d1 and d2) are antiresonant, resulting in much better waveguiding.

FIG. 6(c) is a graph showing transverse mode loss for various waveguide types.

FIGS. 6(d) and 6(e) show waveguide cross-sections for 3D confinement, with 6(d) showing lateral confinement by ARROW layers and 6(e) showing lateral confinement by effective index guiding due to a ridge in top layer.

FIG. 6(f) is an SEM image of a fabricated hollow-core ARROW waveguide with core dimensions are 12 µm by 3.5 µm with a 0.57 µm high and 5 µm wide ridge on top.

FIG. 9(a) shows a near-field setup, where the emission at the output facet is imaged onto a camera. FIG. 9(b) shows a far-field setup, where the waveguide emission is detected several inches away from the facet (far-field) and recorded by scanning a detector perpendicular to the propagation direction.

FIGS. 12(a) and 12(b) illustrate a generic EIT λ-scheme. FIG. 12(a) shows a bare-state basis, and FIG. 12(b) shows a dressed-state basis.

FIGS. 13(a), 13(b) and 13(c) depict linear EIT effects. FIG. 13(a) shows a Lorentzian absorption profile of |1>–|3> transition in absence of coherent coupling, FIG. 13(b) shows an EIT profile in the presence of coherent coupling, where residual absorption on resonance is determined by the coherence dephasing rate $\Gamma_2$. FIG. 13(c) depicts a dispersion profile with (solid line) and without (dashed line) EIT.

FIG. 15(a) depicts an EIT scheme wherein levels |1>–|3> form a Λ-scheme for observation of EIT and slow light. A signal field ($\Omega_S$) on the |2>–|4> transition yields enhanced cross phase modulation of the probe field ($\Omega_P$), where $\Omega_C$ is the coherent coupling field, and $\gamma_i$ are the decay rates. In FIG. 15(b), solid lines represent achievable coherence dephasing rate (left) and group velocity (right) as EIT cell dimensions are reduced. Dashed lines represent values observed in a bulk experiment. FIG. 15(c) depicts limitations of a single photon Kerr phase shift versus EIT cell diameter; 2-photon absorption (dashed line), dephasing induced absorption (dash-dotted line), waveguide loss (circles), and dispersion (solid line) are shown.

FIGS. 16(a) and 16(b) depict how the present invention may be employed to provide integrated optical tweezers.

DETAILED DESCRIPTION OF ILLUSTRATIVE EMBODIMENTS

Overview

Currently, cutting edge optical studies of biological agents such as DNA molecules or cells do not take advantage of the established technologies that have made optoelectronic and photonic integrated circuits so successful. Optical setups for biomedical applications typically involve bulky three-dimensional setups and often times the use of microscope objectives for excitation and/or collection. The main reason behind this fact is the inability to guide light through the media in which the cells and molecules are hosted (typically aqueous solutions or gas phase), as these media have lower refractive indices than the surrounding solid-state material.

Here, we present the invention of a radically different approach to creating an experimental platform for optical studies on non-solid-state materials. By using specially designed multi-layer optical waveguides, it is possible to guide light through low-index media over macroscopic distances which will enable optical devices with both improved and novel capabilities. To our knowledge, such waveguides have never been fabricated to work with non-solid core layers as described herein.

The novelties of this approach compared to state-of-the-art techniques include:
- low-loss guiding of light inside a narrow channel of low-index media (gaseous or liquid) on a semiconductor chip. Low-index in this context means that the refractive index of the sample material is less than any of the indices of the solid-state host material.
- Ability to guide light in the same volume as the low-index material. This allows for transmission, absorption or interference measurements over macroscopic distances.
- Ability to discriminate/filter selective wavelengths along the sample volume. This results from the fact that the waveguide is optimized for a desired wavelength range.
- Entirely planar technology for high sensitivity optical measurements compatible with fiber-optic technology.
- Massive parallelism for multiple measurements on a single chip.
- Potential for further integration with additional optical elements such as photo detectors on the same chip.
- Ability for optical measurements on microchannels of an order of magnitude smaller dimension.
- Specific methods to fabricate hollow-core ARROW waveguides based on sacrificial core layers.
- Platform for realizing large nonlinear phase shifts between light signals using EIT in atoms, e.g., Rb.

Figure 11:
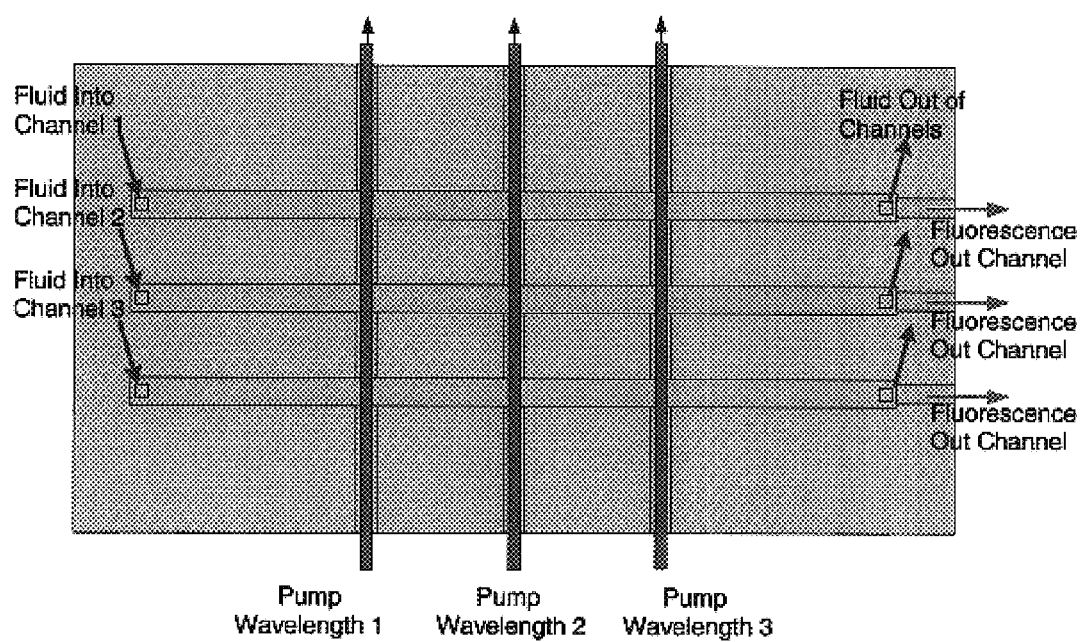
FIG. 11 depicts a top sectional view of an exemplary (3×3 array) parallel optical measurement system based on ARROW waveguide technology in accordance with the present invention.

Shown in the drawings are two images that show an implementation of the invention on a single device level as well as in a highly integrated setting for parallel measurements. These two implementations are shown in FIGS. 4 and 11, respectively.

Figure 1A:
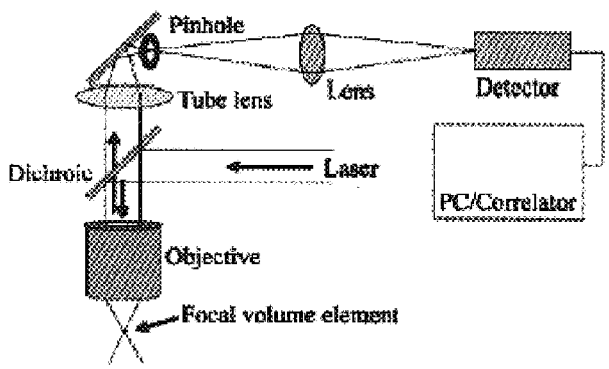
FIG. 1(a) schematically depicts a fluorescence correlation spectroscopy setup in which the sample is placed in the focal volume element.
Figure 1B:
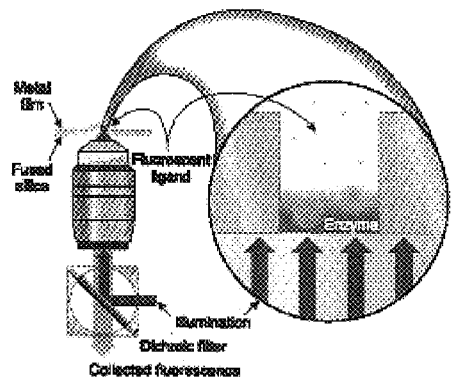
FIG. 1(b) depicts an apparatus for single-molecule enzymology. In both setups, fluorescence is excited and detected perpendicular to the wafer plane, and bulk optics are used.
Figure 2A:
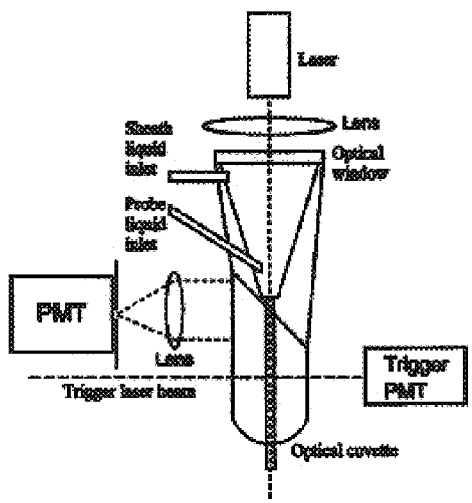
FIGS. 2(a) and 2(b) illustrate flow cytometry setups. In both cases, light cannot be guided along the liquid channel and is detected in the perpendicular direction.
Figure 2B:
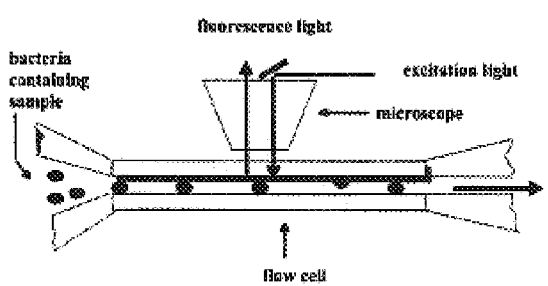
Figure 3A:
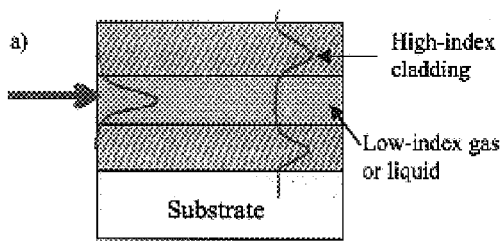
FIG. 3(a) illustrates a conventional microchannel in which low-index materials are surrounded by high-index cladding material, and where light is not guided and leaks into the claddings quickly.
Figure 3B:
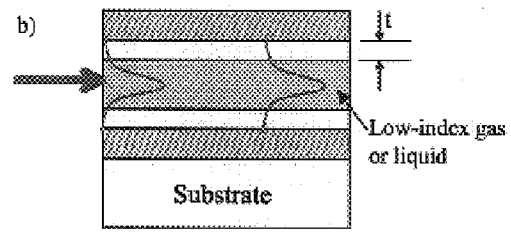
FIG. 3(b) depicts an ARROW waveguide structure in which high-index cladding layers of correct thickness keep light inside the core and enable guiding.
Figure 4A:
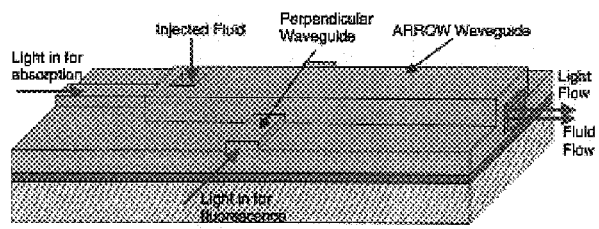
FIGS. 4(a), 4(b), and 4(c) depict an integrated optical measurement platform based on ARROW waveguides, in accordance with the present invention.
Figure 4B:
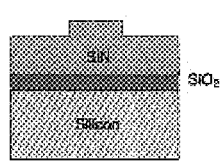
Figure 4C:
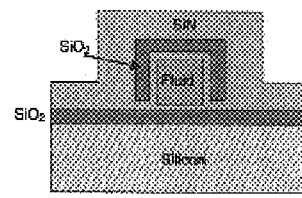

FIGS. 4(a)–(c) show our target sample design using integrated ARROW waveguides that illustrates a number of important advantages and novelties. By using this concept, we will achieve the following improvements over current state-of-the art methods: We can rely on light coupling and collection in the plane of the substrate leading to a compact scalable layout, higher coupling efficiencies of light emitted from a radiating dipole into the waveguide mode and consequently improved sensitivities. We can utilize fiber-optic waveguide coupling into the structures, which is well-developed in optoelectronics and photonics. We will be able to guide light along with the sample inside the chip, which will allow for completely novel experiments such as absorption measurements along the channel as well as simultaneous fluorescence detection and filtering along the direction of the sample flow. Importantly, we will gain the potential for parallel measurements on multiple channels since the excitation beam propagates in a waveguide mode—not as a Gaussian beam with a single focus as is the case in the approaches described above. Finally, ARROW waveguides will permit measurements on smaller volumes for flow cytometry.

Figure 5A:
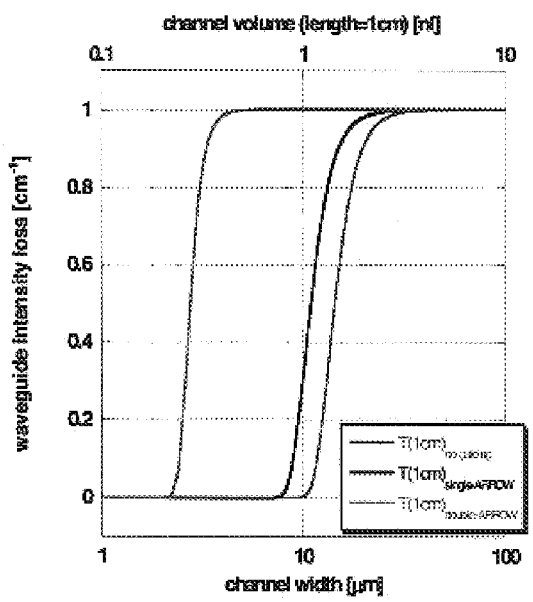
FIGS. 5(a) and 5(b) show comparisons of optical loss and transmission, respectively, in low-index liquids compared to ARROW structures, illustrating that ARROW structures lead to extremely low loss and can be used with smaller sample volumes.
Figure 5B:
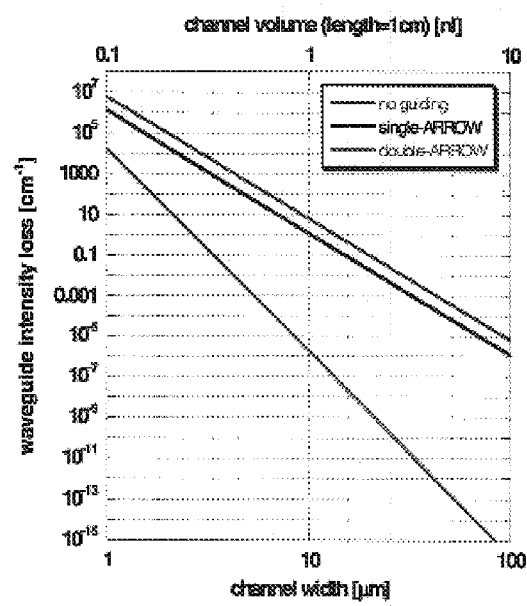

The dramatic effect on flow cytometry is illustrated by FIGS. 5(a) and (b), which compare optical guiding in a conventional microfluidic channel or capillary with two types of ARROW structures to be described in more detail below. FIG. 5(a) shows the propagation loss in $cm^{-1}$ in a structure versus core dimension $\alpha$ (bottom axis) and resulting sample volume (top axis, channel length: 1 cm). It can be seen that losses in a double-ARROW structure are several orders of magnitude lower than in a regular microchannel. As shown in FIG. 5(b), this leads to significantly improved waveguide transmission down to the micron range, which will be sufficient for detecting any bacteria and other cells with dimensions of a few microns.

One goal of ours is to have highly functional, highly parallel structures naturally combined with other integrated elements such as interferometers and detectors on the same chip. The research described herein provides the first crucial steps in this direction: the demonstration of waveguiding in ARROW structures with liquid core layers and the fabrication of simple elements suitable for fluorescence measurements on DNA molecules. We point out that the ARROW principle is well understood and being used in other areas. This will also be the first planar setup relying entirely on techniques successfully used in integrated optics.

As a result of our research, better measurement tools will evolve that will improve both our fundamental understanding of health-related processes in cells and molecules as well as lead to improved flow cytometry methods.

Below we provide a more detailed description of exemplary embodiments and applications of the present invention. The bulk focuses on fluid applications, however, these parts are also applicable to gases. In addition, it should be noted that invention may be carried out with a variety of substrate and waveguide materials, including the materials discussed in connection with the examples described below as well as those listed below (this list is not intended to be exhaustive):

Exemplary substrates:
  Semiconductors (useful for integrating electronic and optoelectronic devices (III–V semiconductors) with the waveguide), including silicon, Ge, diamond, all III–V semiconductors (GaAs, InP, HgCdTe, GaN, GaP, etc.).
  Metals (useful for making a low cost device), including Al, Tin, Titanium, Copper, etc.

Plastics and Polymers (again useful for a low cost device and integrating with electronics on PCB boards). Insulators like ceramic or glass (useful because they produce a transparent substrate or because of heat mitigation).

Silicon based glasses—silica, quartz, soda lime, boron doped, etc.

alumina, sapphire

Exemplary waveguide materials:

Any material possibly deposited by chemical vapor deposition, including silicon dioxide, silicon nitride, silicon oxy-nitride (important because they are very commonly deposited by chemical vapor deposition).

Any material that could be sputtered or evaporated onto a substrate, including silicon dioxide, silicon nitride, and silicon-oxynitride.

Any material that could be spun-on or dip coated including spin-on-glass, polyimides, and polymer based materials.

Exemplary sacrificial layer materials:

Any metal, including aluminum, silver, gold, titanium, tungsten, copper.

Polymer materials, including SU8, photoresist, and polyimide.

DETAILED DESCRIPTION OF EXEMPLARY
IMPLEMENTATIONS AND APPLICATIONS

We will now explain our invention in sufficient detail to enable a person of ordinary skill in the field of integrated optics to make and use the invention without undue experimentation. The following description is not intended (nor would it be possible) to serve as an exhaustive discussion of every possible embodiment, application or method of manufacturing a device within the scope of our invention. It is sufficient, however, to enable the skilled artisan to practice our invention. We will first briefly discuss our preliminary studies and then we will explain a method for fabricating exemplary embodiments of the invention, optical measurements for characterization and testing, a phase-shift device based on electromagnetically induced transparency, and a possible implementation of an integrated "optical tweezers" in accordance with the present invention.

Preliminary Studies

To date, we have fabricated and tested hollow-core ARROW waveguides with both gaseous and liquid cores and demonstrated low-loss propagation through both types.

1. Waveguides with Air Cores

For the design of the hollow-core ARROW waveguides, we chose cladding materials that are compatible with silicon microfabrication and offer the best potential for further integration. Hence, the transverse profile of the waveguide consists of alternating layers of silicon nitride and oxide (n=2.1 and 1.46, respectively, see FIG. 6(b)). The required thicknesses $d_i$ for the i-th cladding layer of the required Fabry-Perot reflector at our design wavelength of 785 nm can be determined in the same way as for an all-solid ARROW waveguide and are given by $$d_i = \frac{\lambda}{4n_i}(2N+1)\left[1 - \frac{n_c^2}{n_i^2} + \frac{\lambda^2}{4n_i^2 d_c^2}\right]^{-0.5} \quad (1)$$

where $n_i$ and $n_c$ are the cladding and core refractive indexes, respectively. For $n_c$=1 (air), this results in layers of 109 nm (SiN) and 184 nm (SiO$_2$) in the lowest order (N=0). One advantage of the ARROW approach is that the layers do not have to be periodic. As long as the correct $d_i$ for a given material is chosen that layer will reduce the propagation loss. FIG. 6(c) shows the calculated transverse power propagation loss as a function of core thickness $d_c$ for different structures. The black line represents the loss without ARROW confinement, i.e., an air core surrounded by a silicon nitride layer, and shows that propagation in cores with diameters less than 20–30 µm is not feasible. FIG. 6(c) shows the loss for the case where the ARROW cladding consists of one silicon nitride and one air layer on each side of the core, which reduces the loss drastically. However, incorporating two more air layers poses severe fabrication problems. FIG. 6(c) also shows the loss if periods of alternating oxide and nitride layers are used. Each additional period reduces the loss by a factor of approximately 3. Clearly, a tradeoff exists between reduction in waveguide loss and fabrication complexity. We chose to fabricate structures with three top and bottom periods which result in a transverse mode loss of 1.1 cm$^{-1}$ for $d_c$=3.5 µm (dash-dotted line).

The second important design consideration is the realization of lateral confinement for effective single mode propagation. We analyzed different types of lateral confinement. FIG. 6(d) shows a rectangular core with uniform cladding layers where all confinement is realized using the ARROW principle. FIG. 6(e) shows a similar structure that includes an optimized etch of the top SiO$_2$ layer to enable effective index confinement in the lateral direction. In this case the mode would be confined to a narrower area underneath the ridge and somewhat lower propagation loss is possible. However, 2D loss simulations show that the etch depth has to be controlled very carefully (within a few nm), which poses additional fabrication challenges.

After determining the structure for lowest loss, two major issues were addressed in order to fabricate the waveguides: The first was finding a suitable sacrificial core layer with lateral dimensions on the order of microns and lengths up to several centimeters. The second issue was growing sufficiently thick top layers over the hollow core to provide mechanical stability.

FIG. 6(f) shows an SEM micrograph of a completed hollow-core ARROW waveguide using the following process steps, which are represented generally by FIGS. 7(a)–7(d):

1) Alternating oxide and nitride layers were deposited on a silicon substrate using plasma-enhanced vapor deposition (PECVD) to form the bottom cladding layers. Deposition was carried out at temperatures between 250° C. and 300° C. Deposition rates for nitride and oxide layers were 70 Å/min and 200 Å/min, respectively. See FIG. 7(a).
2) Subsequently, a 3.5 µm thick photosensitive polyimide (SU-8) layer was deposited on the substrate and then patterned into 2 cm-long ridges of varying width (6–50 µm). See FIG. 7(b).
3) The top ARROW layers and a 2.944 µm SiO$_2$ cap layer for mechanical stability were grown. The thickness of the top layer was chosen such that it provides additional confinement according to eqn. (1). See FIG. 7(c).
4) To create the hollow waveguide cores, the sacrificial SU-8 layer was removed using a solution of H$_2$O$_2$ and H$_2$SO$_4$ at 85° C. providing the required high directional etch selectivity. A photoresist ridge was then patterned on top of the waveguide and transferred into the top SiO$_2$ layer using CF4 based plasma etching. (It should be noted that one can do this processing using different materials as sacrificial layers, such as metals (aluminum), polyimides (SU-8), and photoresist.) This ridge was added to evaluate the possibility for lateral confinement. As can be seen from FIG. 7(d), almost perfectly rectangular cores with excellent smoothness can be fabricated using this method.

Figure 6G:
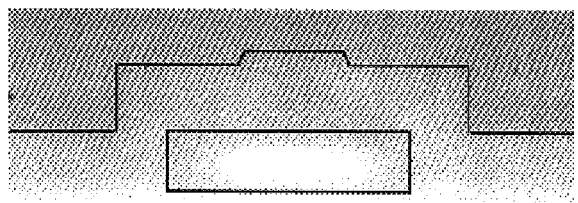
FIG. 6(g) depicts an output facet image of a mode propagating in a hollow ARROW waveguide, with black lines outlining the sample for clarity.
Figure 6H:
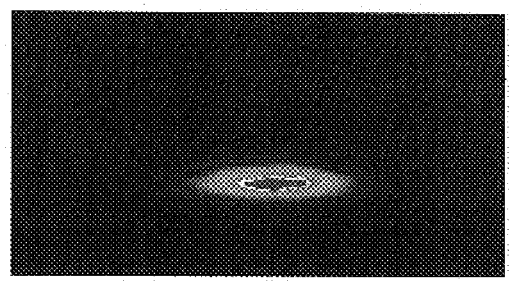
FIG. 6(h) shows a near-field intensity mode profile.

The completed samples were cleaved into 0.5–8 mm long waveguides and light from a diode laser at 785 nm with 0.25 mW power was coupled into the structures. The near-field image of the mode profile at the output facet was recorded using magnifying optics (0.85 NA lens, 60:1 magnification) and a CCD camera (BeamPro Model 2320, Photon Inc.) while simultaneously illuminating the output facet to image both facet and ARROW mode directly. For the first time, low loss propagation through an integrated ARROW waveguide with a hollow air core was observed. The mode image is shown in FIG. 6(g) for a waveguide with 12 μm core width, 3.5 μm core height, and 2 mm length (same dimensions as FIG. 6(f)). The black lines outline the facet of the waveguide since the microscope image is not as clear as the SEM micrograph. The optical mode (bright ellipse) is clearly confined inside the hollow air core. In FIG. 6(h) the intensity profile of the ARROW core mode is shown. A single mode (fundamental ARROW mode) is observed. The intensity FWHMs of the mode are 1.32 μm (transverse direction) and 6.4 μm (lateral), respectively. This corresponds to a mode area of 6.64 μm². To our knowledge, this is the smallest optical mode observed in air to date.

Figure 6I:
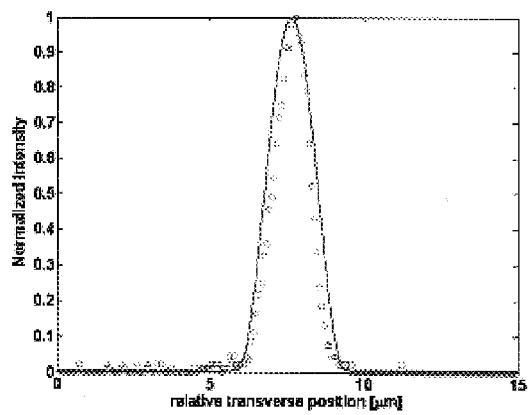
FIGS. 6(i) and 6(j) provide a comparison of observed transverse and lateral mode profiles (circles) with theoretical calculation (lines).
Figure 6J:
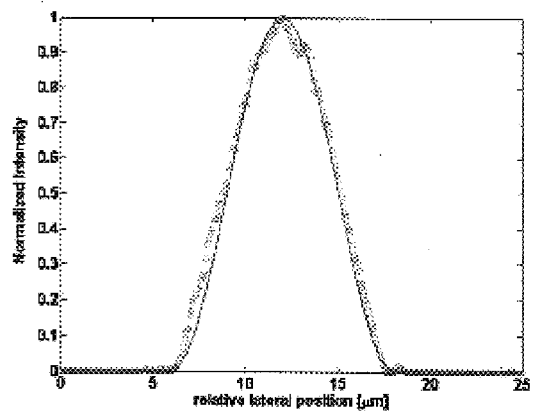

FIGS. 6(i) and 6(j) show the transverse and lateral cross sections through the center of the waveguide (circles) in comparison with the theoretically expected profile (solid line) of the fundamental ARROW mode according to our design specifications. For the lateral mode calculation the structure was assumed to have no etched ridge in the top $SiO_2$ layer. No fitting parameters were used and the agreement between theory and experiment is excellent. FIG. 6(g) also demonstrates that the lateral confinement results from the vertical ARROW layers rather than the ridge in the top $SiO_2$ layer as effective index guiding would have led to a narrower mode.

Figure 6K:
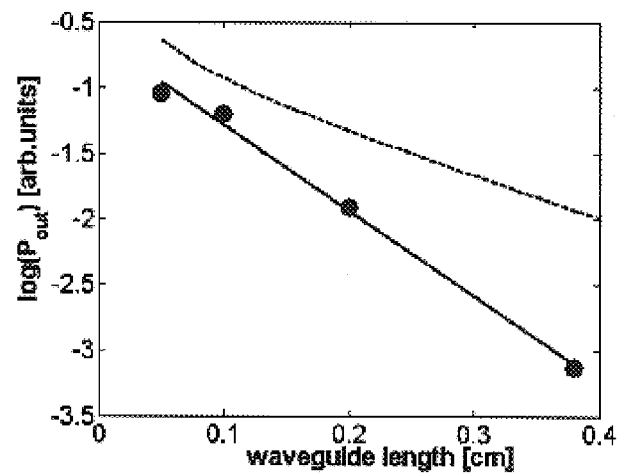
FIG. 6(k) is a graph of waveguide loss versus waveguide length. Circles: experiment, line: exponential fit.
Figures 7A, 7B, 7C, 7D:
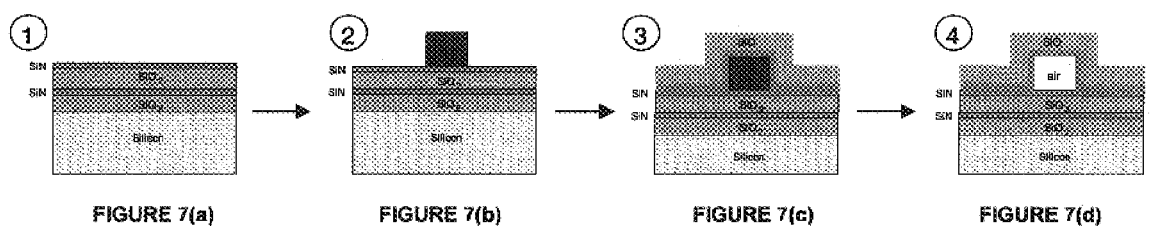
FIGS. 7(a), 7(b), 7(c) and 7(d) depict steps of a fabrication process in accordance with the present invention.
Figure 8A:
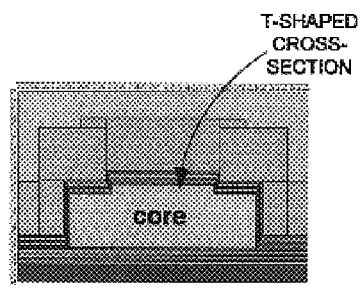
FIGS. 8(a), 8(b) and 8(c) respectively depicts structures like those depicted in FIGS. 7(a)–(f) but showing that the non-solid core may be made with different cross-sectional shapes, including T-shaped, rectangular, and semi-circular.
Figure 8B:
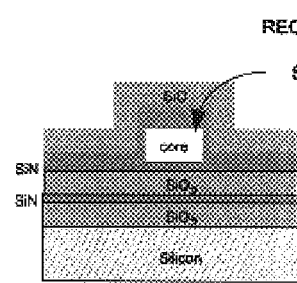
Figure 8C:
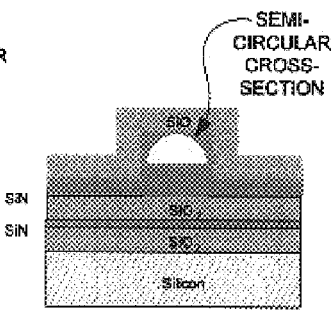
Figure 9A:
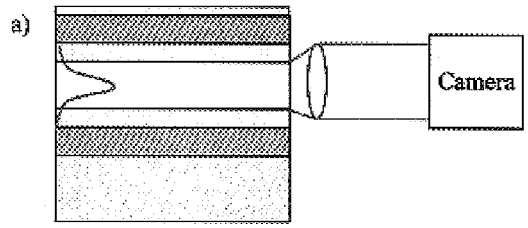
FIGS. 9(a) and 9(b) depict waveguide characterization setups.
Figure 9B:
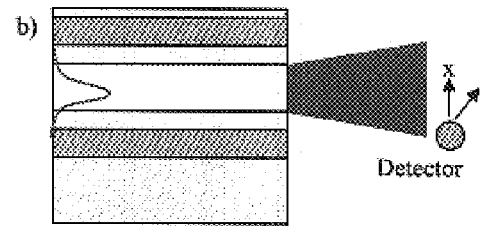
Figure 10:
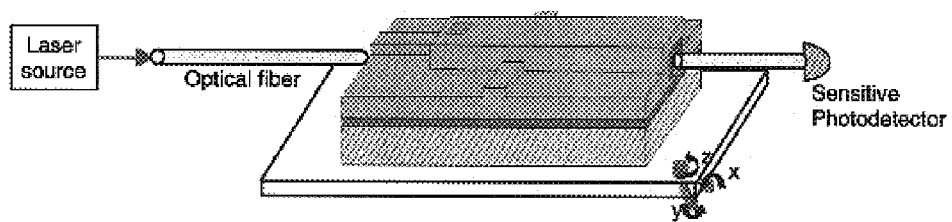
FIG. 10 depicts an absorption measurement setup for an ARROW waveguide, wherein an optical connection to the sample is made with conventional fiber optic techniques within the wafer plane.

The waveguide loss of the ARROW structure was determined by recording the transmitted power as a function of waveguide length (input polarization along y). The result is shown in FIG. 6(k) for a waveguide with a lateral width of 24 μm. By fitting the data to an exponentially decaying line, a waveguide loss of 6.5 cm$^{-1}$ was deduced. For comparison of this value to theoretical expectations, coupling of several modes into the core was taken into account. Since the fiber is aligned to the waveguide center, the light is coupled predominantly into odd ARROW modes. The coupling coefficients $\beta_i$ and loss values $\alpha_i$ (calculated with commercial 3D mode solver FIMMWAVE) for the first, third and fifth mode are 28.6%, 15.3%, 12.6% and 3.29 cm$^{-1}$, 21.79 cm$^{-1}$, and 64.37 cm$^{-1}$, respectively. The expected output intensity is $$I_{out} \propto \beta_1 e^{-\alpha_1 L} + \beta_3 e^{-\alpha_3 L} + \beta_5 e^{-\alpha_5 L}$$

and the resulting curve is shown in FIG. 6(k) as dashed line with an average loss of 3.7 cm$^{-1}$. The remaining discrepancy between theory and experiment is due to scattering losses and thickness fluctuations of the ARROW confinement layers, especially in lateral direction. The magnitude of the loss is mainly given by loss in lateral (y) direction. There are several ways to reduce the loss significantly in the future. These include lateral variations of the core thickness as has been used for large area hollow waveguides with metal claddings, additional ARROW layers, or the use of semicircular core shapes which can be achieved using a modified sacrificial layer process.

2. Liquid Cores:

Here, we designed a waveguide with layers of 110 nm (SiN) and 281 nm (SiO2) for low loss propagation in water (n=1.33) at 690 nm. This optimizes the structure for fluorescence emission of dye molecules that are excited by a He—Ne laser at 635 nm. The waveguides were fabricated in the same way as for air cores.

For optical characterization, the samples were cleaved into waveguides with variable length (0.5 to 8 mm) and light from a He—NE laser at 635 nm or a diode laser at 785 with up to 1 mW power was coupled into the waveguide cores using single-mode fiber. For measurements with liquid cores, the cores were filled with ethylene glycol and then mounted on a translation stage for transmission measurements. Ethylene glycol (n=1.43) was used instead of water because it evaporates more slowly and allows for longer measurement times.

The near-field image of the mode profile at the output facet was recorded in the same way as for the air core sample and led to the same results, i.e., observation of a confined and propagating mode inside the non-solid ARROW waveguide core.

The waveguide loss was determined by measuring the intensity throughput as a function of waveguide length. By fitting the data to a decaying exponential, a loss of 2.4 cm$^{-1}$ is observed at 635 nm for a sample with core width 24 μm. At 785 nm, we could not observe any transmission, which implies a loss of at least 10 cm$^{-1}$ based on the current sensitivity of our setup. The experimental values are in qualitative agreement with the expectation of higher loss at longer wavelengths and the discrepancy is mainly due to contributions from coupling into higher order ARROW modes with significantly higher loss and scattering losses in the waveguide. We emphasize that the wavelength dependence of the loss is strong and can effectively be used to suppress propagation at certain wavelengths. In addition, this dependence can be tailored by choosing the ARROW layer thicknesses while maintaining low loss at one design wavelength. This wavelength selectivity makes these waveguides especially attractive for fluorescence and Raman scattering applications where filtering of a pump beam from a signal at longer wavelengths is required. Together with the high coupling efficiency of fluorescence into the ARROW mode, this feature makes liquid core ARROW waveguides ideally suited for optical measurements with single molecule resolution.

Based on the preliminary results on single waveguides described above, ARROW waveguides with non-solid cores can be used for highly parallel sensor architectures with multiple ARROW sensor waveguides on the same chip. A possible implementation of such a device is shown in FIG. 11. In this top view, three ARROW channels are shown into which sample fluids can be injected using microfluidic connections. One implementation would use PDMS structures over a liquid reservoir that is connected to the actual optical waveguide. Liquids are injected into these reservoirs using syringes. The ARROW waveguides can be intersected by conventional optical waveguides to couple excitation light for fluorescence or Raman scattering into the sample channel. The advantage of this technology is that several pump waveguides can cross a single ARROW channel and that a single pump waveguide can intersect multiple ARROW channels to excite fluorescence in more than one sample volume. This leads to highly connected, parallel sensor architectures. The pump waveguides are realized in $SiO_2$ using conventional index waveguiding. In another implementation, the excitation could occur via the ARROW waveguides and collection through the conventional waveguides.

Electromagnetically Induced Transparency (EIT)

Electromagnetically induced transparency (EIT) is a topic that has fascinated researchers for more than a decade. It is an optical quantum interference phenomenon that is based on Fano interference (Fano, U., *Phys. Rev.* 124, 1866, (1961)) and is extremely interesting from a quantum electronics and quantum optics point of view. Over the course of time, EIT-related research has advanced our knowledge about the limits of light-matter and light-light interactions tremendously. For example, the common notion that population inversion is a fundamental requirement for laser action had to be revised after the seminal papers by Harris (Harris, S. E., "Lasers without inversion: interference of lifetime-broadened resonances," *Phys. Rev. Lett.* 62 1033 (1989)) and Scully (Fill, E. E. et al., "Lasing without inversion via the lambda quantum-beat laser in the collision-dominated regime," *Opt. Comm.* 77 36 (1960)) and the actual demonstration of an inversionless laser by Padmabandu et al. (Padmabandu, G. G. et al., "Laser oscillation without population inversion in a sodium atomic beam," *Phys. Rev. Lett.* 76 APS, 2053 (1996)). Other applications in quantum optics include photon blockade in a high-finesse cavity (Imamoglu, A. et al., "Strongly interacting photons in a nonlinear cavity," *Physical Review Letters* 79 1467 (1997)) or electromagnetically induced opacity for photon pairs (Resch, K. J. et al., "Electromagnetically induced opacity for photon pairs," *Journal of Modern Optics* 49 487 (2002)). Extensions to basic research in quantum information processing based on slow light are also conceivable (Rostovtsev, Y. et al., "Slow, ultraslow, stored, and frozen light," *Optics & Photonics News* 13 44 (2002)). EIT can occur in media that exhibit the three-level scheme ("λ-scheme") depicted in FIG. 12(a) that are subjected to two optical fields, a coherent coupling field (Rabi frequency $\Omega_C$) and a (typically weak) probe field ($\Omega_P$). As mentioned above, FIGS. 12(a) and 12(b) illustrate a generic EIT λ-scheme, with FIG. 12(a) showing a bare-state basis, and FIG. 12(b) showing a dressed-state basis.

The required characteristics of the scheme to observe EIT are the following: The highest level (state |3>) is coupled to a continuum of states and in addition has dipole-allowed optical transitions to state |2> and ground-state |1>. In Fano interference, asymmetric absorption line shapes characteristic for the effect arise from the superposition of transition amplitudes from the ground state to a continuum via a direct transition or a transition through state |3> (Fano, U., *Phys. Rev.*, 124 1866 (1961)). In EIT, a strong coherent coupling field applied on the |2>–|3> transition creates superposition states ("dressed states" |2d> and |3d>) whose splitting depends on the Rabi frequency $\Omega_C$ (intensity) of the coherent coupling field. Interference in this case results from a superposition of amplitudes for transitions from the ground state to the continuum through the two bound dressed states. As a result, a lifetime-broadened transition between |1> and |3> characterized by a Lorentzian absorption profile (FIG. 13(a)) is changed to an EIT absorption profile (FIG. 13(b)) with an interference-induced absorption minimum for vanishing two-photon detuning (identical detuning of $\Omega_C$ and $\Omega_P$ from level |3>).

Another interpretation of the phenomenon is that of coherent population trapping (CPT) (Gray, H. R. et al., "Coherent trapping of atomic populations," *Opt. Lett.* 3 218 (1978)) in the bare-state basis (states |1>, |2>, |3>). It can be shown that the combined atom-light-field system has a so-called "dark state", i.e., an eigenstate of the total Hamiltonian that is time-invariant and hence does not lead to absorption. The dark state is a coherent superposition between the lower states and given by $|d\rangle \sim \Omega_C|1\rangle - \Omega_P|2\rangle$ where the phase relation (expressed in the minus sign) is essential.

The interference does not only appear in absorption (the imaginary part of the linear susceptibility X=X'+i X"), but also appears in the real part (dispersion) and higher order nonlinear susceptibilities ($X^{(2)}$, $X^{(3)}$, . . . ). The dispersion modification is illustrated in FIG. 13(c). The strongly increased dispersion (slope) at the EIT resonance translates to a reduction in the group velocity of a light pulse. Nonlinear interference effects are especially interesting as the nonlinear susceptibility can be significantly increased while preserving the linear transparency. This means that full advantage of the nonlinear optical coefficients can be taken without suffering from linear absorption of the fields. This can be used for efficient sum-frequency generation (Harris, S. E. et al., "Nonlinear optical processes using electromagnetically induced transparency," *Phys. Rev. Lett.* 64 1107 (1990)) or the generation of giant third-order Kerr nonlinearities for phase modulation purposes (Schmidt, H. et al., "Giant Kerr nonlinearities using electromagnetically induced transparency," *Opt. Lett.* 21 1925 (1996); (Schmidt, H. et al., "High-speed properties of a phase-modulation scheme based on electromagnetically induced transparency," *Optics Letters* 23 1007 (1998)).

The key requirements for EIT that need to be kept in mind for choosing or designing an EIT system are the following: It is clear from the expression for the dark state |d> that maintaining coherence is of crucial importance for the observation of the EIT effect. A density-matrix approach shows that the coherence dephasing rate $\gamma_{12}$ between states |1> and |2> needs to be as small as possible. Therefore, systems with small values of $\gamma_{12}$ need to be identified. In the absorption profile (FIG. 13(b)) the minimum absorption is proportional to $\gamma_{12}$ and the splitting is determined by $\Omega_C$. In order to observe the interference dip, the condition $\Omega_C^2 > \gamma_{12}\Gamma_3$ needs to be fulfilled, setting a lower limit for $\Omega_C$. In addition, the simple expressions given above assume a purely lifetime broadened upper state |3>, but neglected any additional broadening mechanisms, which will reduce the magnitude of the interference effects. This includes inhomogeneous broadening mechanisms such as Doppler or crystal field broadening and homogeneous broadening mechanisms such as interface roughness scattering in semiconductors (see below).

EIT has been observed in different types of media and in the following section we summarize the most relevant approaches with special attention to their strengths and limitations.

Other Approaches to Quantum Optics on a Chip

Very recently, researchers have started to develop experimental platforms to perform quantum optical experiments on the surface of a chip using mechanisms to trap, manipulate, and move atoms (Bartenstein, M. et al., "Atoms and Wires: Toward Atom Chips," *IEEE Journal of Quantum Electronics* 36 1364 (2000); Hansel, W. et al., "Bose-Einstein condensation on a microelectronic chip," *Nature* 413 498 (2001)). In addition, the use of quantum coherence for the realization of atomic clocks has been proposed (Kitching, J. et al., "Miniature vapor-cell atomic-frequency references," *Appl. Phys. Lett.* 81 553 (2002)). This shows that the knowledge acquired from integrating EIT with a semiconductor chip will influence non-EIT-based research and science as well.

Proposed Approaches

The discussion above has made it clear that ideally we would like to have an EIT medium with the optical qualities of alkali vapor atoms and the practical advantages of a semiconductor. Since no single medium seems to exist that inherently combines both features, we propose a way to actually use alkali atoms, but integrate them on a semiconductor chip as a host medium. The advantages inherent to such an approach are:

maximum interference: By creating atomic vapor-containing cavities on a chip whose properties are comparable to bulk cells, interference effects can be realized with maximum strength.

compact size: Most, if not all of the bulk optics are unnecessary. All that is required is to couple light into the waveguide, which can be done with standard fiber optics methods. The length of the Rb-cavity can easily be varied between nanometers and millimeters.

simplicity: The amount of required alignment is significantly reduced, making such an EIT-chip much more robust to environmental impact. For example, beam splitters can be realized with 3 dB waveguide couplers, standard waveguiding methods ensure automatic alignment of the beams with the Rb cavity, etc. If source and detector are integrated on the chip, there is absolutely no alignment necessary.

versatility: The large available suite of microprocessing techniques opens the possibility to add more complex controls to an EIT structure. For example, electrical contacts can be lithographically defined to apply electric fields or pass current to generate precise magnetic fields at the cavity location. Other examples include straightforward and accurate temperature control.

scalability: Once the fabrication method has been developed for one cavity, it is easily possible to define multiple cavities on the same chip, which could serve different purposes.

A comprehensive program to realize such integrated structures needs to address several areas: These are sample design and simulations, development of suitable fabrication methods, building a spectroscopy setup, and testing of structures and devices. The following approaches to address these issues are described.

Materials and Waveguide Design

One of the main new contributions of this work is the insertion of a low index (essentially air) gap into a (ideally single-mode) waveguide structure. A main consideration is to choose a suitable material system in which to realize the waveguides. The material system needs to have the following properties:

guiding of light at the atomic transmission wavelength (e.g., 795 nm for the D-line in Rb)

allow for design of single-mode waveguide structures allow for etching cavities for integrated Rb-cell allow for integration with other optoelectronic and photonic elements Antiresonant Waveguide (Arrow) Structures on Silicon Non-solid core ARROW waveguides are ideally suited for realizing longer cavities in combination with single-mode waveguides. As described above, if the layer thicknesses are chosen such that the thickness of a low-index core and a high-index cladding are $m\lambda/2$ and $(2\,m+1)\lambda/4$, respectively, light propagation occurs in the low-index layer and the structure forms a so-called antiresonant reflecting optical waveguide (ARROW) Duguay, M. A. et al., "Antiresonant reflecting optical waveguides in $SiO_2$—Si multi-layer structures," *Appl. Phys. Lett.* 49 13 (1986); Koch, T. L. et al., "Antiresonant reflecting optical waveguides for III–V integrated optics," *Elec. Lett.* 23 244 (1987).

This concept can be used to our advantage by fabricating an ARROW structure where air is the low-index core in which light propagation occurs. Since the index of the Rb cavity is similar, the wave will remain confined in this region and diffraction and coupling losses are significantly reduced. A thin transmissive wall of silicon would separate the air core from the Rb cell. While MEMS-based methods can be used to realize ARROW structures for integrated optics (Nathan, A. et al., "Silicon integrated optic devices and micromechanical sensors based on ARROW," *Proc. SPIE* 2686 2 (Integrated Optics and Microstructures III, San Jose, Calif.) (1996)) and ARROW structures can be integrated with photodetectors on the same chip (Benaissa, K. et al., "IC compatible optical coupling techniques for integration of ARROW with photodetector," *J. of Lightwave Technology* 16 1423 (1998)), the fabrication of such a structure is more challenging than the simpler slab waveguides.

Optical Spectroscopy

Figure 14:
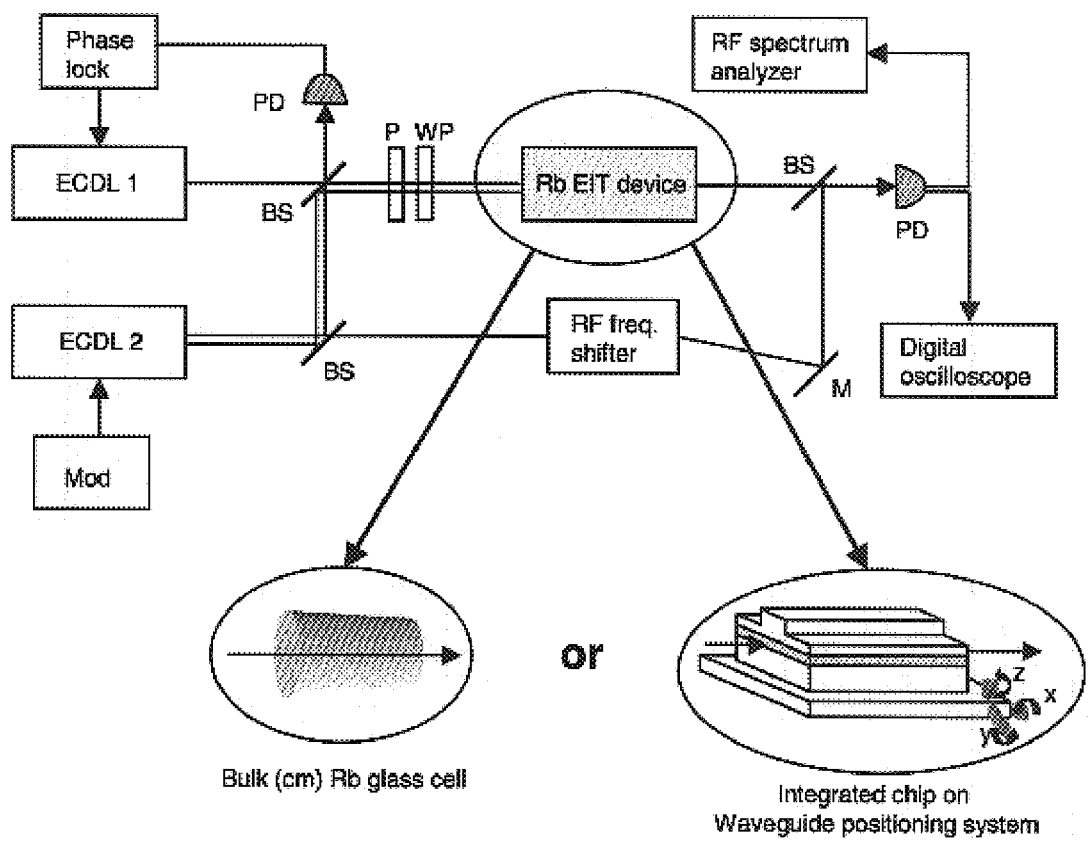
FIG. 14 illustrates a spectroscopy system for EIT-on-chip measurements. (Note the following notation: ECDL1/2 refers to external cavity diode lasers. Mod refers to electro-optic modulator. Phase lock refers to microwave frequency. PD refers to high-speed photodiodes. BS refers to beam splitters, P to polarizers, WP to waveplates, and M to mirrors.)

While an ultimate goal is to integrate as many functional elements of the optical setup as possible on one chip, initially the feasibility of the concept of integrating EIT on a semiconductor wafer needs to be demonstrated in a 'standard' bulk EIT setup that is only partially modified. This system, which is shown in FIG. 14, should possess the following capabilities:

The centerpiece of the setup is the active optical element containing Rb vapor of controlled density in which EIT effects occur. First, a conventional bulk glass cell (Kasapi, A. et al., "Electromagnetically induced transparency: propagation dynamics," *Phys. Rev. Lett.* 74 2447 (1995)) will be used to establish and calibrate the spectroscopy setup. Subsequently, the cell will be replaced with the integrated atomic-cavity waveguide chip, which is placed on a suitable micropositioning stage with the option for fiber input and output coupling.

We are currently establishing the capability to carry out spectroscopy in Rb atoms using an external cavity diode laser and a bulk vapor cell. Before performing spectroscopy on integrated EIT structures, we will test the microfabricated cavities for agreement with the simulations and capability of measuring non-EIT rubidium absorption.

Finally, measurements carried out on EIT elements and devices will be analyzed and theoretically modeled using the semiclassical theory for EIT.

Applications of EIT-Related Effects

There are numerous potential uses for devices that can be built using EIT-related effects. We believe the most promising ones will be based on reduced group velocity (slow light), stopped light, and cross-phase modulation between laser fields at very low intensities. This effect can be used to realize optical buffers or storage elements. For instance, a delay of 1 μs can be achieved over a distance of 50 μm assuming a group velocity of 50 m/s. The modified linear dispersion can also be used for highly sensitive magnetometers (Scully, M. O. et al., "High-sensitivity magnetometer based on index-enhanced media," *Phys. Rev. Lett.* 69 1360 (1992)).

Another possibility—discussed in greater detail below— is the use of giant Kerr nonlinearities (Schmidt, H. et al., "Giant Kerr nonlinearities using electromagnetically induced transparency," *Opt. Lett.* 21 1936 (1996)) to realize all-optical cross phase modulators, which are very sensitive to very low levels of light field intensity.

More variations and new applications will arise once the technology has been developed. One can think, for example, about increasing the finesse of the EIT cavity by suitably coating its facets and explore cavity-related EIT effects (Imamoglu, A. et al., "Strongly interacting photons in a nonlinear cavity," *Physical Review Letters* 79 1467 (1997); Lukin, M. D. et al., "Intracavity electromagnetically induced transparency," *Opt. Lett.* 23 295 (1998)).

Below we discuss a specific application, namely, an optical phase modulator

EIT in Alkali Atoms Integrated on a Semiconductor Chip; Single-Photon Phase Shifts We will now discuss the integration of electromagnetically induced transparency (EIT) in alkali atoms on a semiconductor chip. Below, we derive the scaling laws and limitations for the reduction in group velocity and single-photon phase shifts, and we show that miniaturization can lead to large enhancement of single-photon cross-phase modulation for light fields that are confined and guided in an integrated vapor cell. We propose the use of ARROW waveguides with hollow cores to realize the necessary waveguiding capability. The observation of light propagation in waveguides with micron-sized air cores demonstrates the feasibility of this approach.

Electromagnetically induced transparency (EIT) is an optical quantum interference effect that leads to dramatic changes in the optical properties of a medium. These include transparency of an otherwise opaque medium (S. Harris, "Electromagnetically induced transparency", Physics Today, p. 36, July 1997, and references therein), lasing without population inversion (G. G. Padmabandu, G. R. Welch, I. N. Shubin, E. S. Fry, D. E. Nikonov, M. D. Lukin, M. O. Scully, "Laser oscillation without population inversion in a sodium atomic beam", Phys. Rev. Lett. 76, 2053 (1996)), slow and stopped light (M. M. Kash et al., "Ultraslow group velocity and enhanced nonlinear optical effects in a coherently driven hot atomic gas", Phys. Rev. Lett. 82, 5229 (1999); A. V. Turukhin et al., "Observation of ultraslow and stored light pulses in a solid", Phys. Rev. Lett., 88, 023602, (2002)), and enhanced nonlinear effects such as four-wave mixing, sum-frequency generation (S. E. Harris, J. E. Field, A. Imamoglu, "Nonlinear optical processes using electromagnetically induced transparency", Phys. Rev. Lett., 64, 1107 (1990)), and cross-phase modulation (H. Schmidt and A. Imamoglu, "Giant Kerr nonlinearities using electromagnetically induced transparency", Opt. Lett., 21, 1936, (1996)).

Figure 15A:
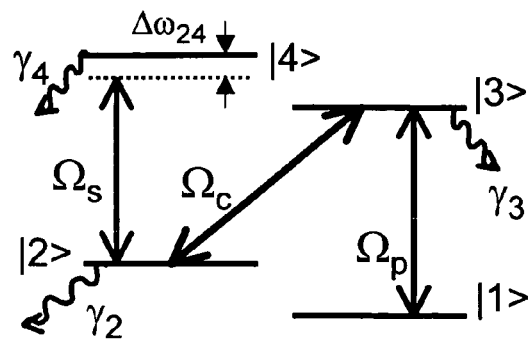
FIGS. 15(a), 15(b) and 15(c) are referenced below to help explain how EIT may be effected in alkali atoms integrated on a semiconductor chip, and how this may be utilized to shift the phase of a photon.

These effects are typically observed in the three-level Λ-scheme shown in FIG. 15(a) that exhibits giant Kerr nonlinearities when including a fourth level. A probe (Rabi frequency $\Omega_P$) and a strong coherent coupling field ($\Omega_C$) create a dark state that effectively decouples the electrons from state |3> resulting in quantum interference effects. The application of an additional signal field ($\Omega_S$) on the |2>–|4> transition leads to enhanced Kerr nonlinearities that result in strong and observable interaction between single photons (A. Imamoglu, H. Schmidt, G. Woods and M. Deutsch "Strongly interacting photons in a nonlinear cavity", Phys. Rev. Lett., 79, 1467, (1997)). This effect has been analyzed by several groups (H. Schmidt and A. Imamoglu: "High-speed properties of a phase-modulation scheme based on electromagnetically induced transparency", Opt. Lett. 23, 1007 (1998); S. E. Harris, and L. V. Hau, "Nonlinear optics at low light levels", Phys. Rev. Lett., 82, 4611, (1999); M. D. Lukin, and A. Imamoglu, "Nonlinear optics and quantum entanglement of ultraslow single photons", Phys. Rev. Lett., 84, 1419, (2000)). Harris and Hau found that in the absence of other nonidealities the obtainable single photon phase shift is limited by dispersion-induced walkoff between the probe and signal pulse with a maximum value inversely proportional to the cross sectional area of the light field. Even larger EIT effects should, therefore be observable in integrated waveguide structures where the optical mode volume is small and overlap with the sample medium is maximized. Other advantages of an integrated platform include robustness, easy alignment and possibility of multiple cells and beam geometries on the same device. Various approaches towards integrated EIT have been taken. EIT in III–V semiconductors was demonstrated (H. Schmidt, K. L. Campman, A. C. Gossard and A. Imamoglu., "Tunneling induced transparency: Fano interference in intersubband transitions", Appl. Phys. Lett., 70, 3455, (1997). J. Faist, F. Capasso, C. Sirtori, K. West, and L. Pfeiffer, "Controlling the sign of quantum interference", Nature, 390, 589, (1997)), but large coherence dephasing rates led to small effects. Results in doped crystals are impressive (A. V. Turukhin et al., "Observation of ultraslow and stored light pulses in a solid", Phys. Rev. Lett., 88, 023602, (2002)); however, these materials are not suitable for integrated optical devices. Here, we propose and analyze the realization of EIT in hot alkali vapor integrated on a semiconductor chip. This maximizes the magnitude of the effects through the small dephasing rates in alkali atoms and the reduced cross section of the optical mode in a waveguide. We analyze the size dependence of the major effects of interest (slow light and single photon phase shifts) and show that under realistic conditions single photon phase shifts are large enough for experimental observation. We propose a way of implementing such integrated EIT waveguide devices using ARROW waveguides with hollow cores and demonstrate light propagation through air in these waveguides with cross sections as small as 25 μm². We remark that size-reduction of vapor cells has been suggested in the context of atomic clocks (J. Kitching, S. Knappe, and L. Hollberg, "Miniature vapor-cell atomic-frequency references", Appl. Phys. Lett. 81, 553 (2002)). However, the dimensions considered were on the order of 1 mm and no concrete fabrication process was described. Here, we discuss cell dimensions as small as a few microns in diameter that allow for single-mode propagation which is especially relevant for phase modulation experiments.

In order to analyze the size dependence of integrated EIT, we consider a cylindrical rubidium cell of length L and cross section A. The magnitude of EIT effects generally increases with decreasing coupling Rabi frequency $\Omega_C$. The minimum $\Omega_C$ value, in turn is determined by the dephasing rate $\gamma_{12}$ for the electrons in the dark state. Unlike in the case of ultracold alkali atoms, coherence dephasing can not be neglected here. It increases strongly as the cell dimensions shrink due to collisions of the rubidium atoms with the cell walls. We model this behavior by considering a cell with coated walls and an inert buffer gas to reduce the probability of dephasing events. According to J. Vanier, et al., the dephasing rate is given by $$\gamma_{12} = \frac{\pi^3}{An_C} D_0 \frac{p_0}{p} + \sigma_2 N_0 v_r \frac{p}{p_0}$$

where $n_C$: number of wall collisions until dephasing occurs, p ($p_0$): buffer gas (atmospheric) pressure, $D_0$: Rb diffusion constant at $p_0$, $N_0$: number of buffer gas molecules at $p_0$, $\sigma_2$:

cross section for Rb-buffer gas collisions, $v_r$: relative velocity of Rb (for values after J. Vanier, et al., see FIG. 15(b)). The size dependence is introduced in the first term, which describes the effect of wall collisions. From $\gamma_{12}$ we determine the acceptable coupling Rabi frequency by setting $\Omega_C^2 \geq 3\gamma_{12}(\gamma_3 + \Delta_D)$ where $\Delta_D$ is the Doppler broadening. For all calculations we assume used in the slow light experiment by Kash (M. M. Kash et al., "Ultraslow group velocity and enhanced nonlinear optical effects in a coherently driven hot atomic gas", Phys. Rev. Lett. 82, 5229 (1999)). From $\Omega_C$ the group index $n_g$ and the group velocity $v_g = c/n_g$ can be determined as $$v_g = \frac{8\pi}{3N\lambda^2} \frac{[\gamma_{12}(\gamma_3 + \Delta_D) + \Omega_C^2]^2}{\gamma_r \Omega_C^2}$$

Figure 15B:
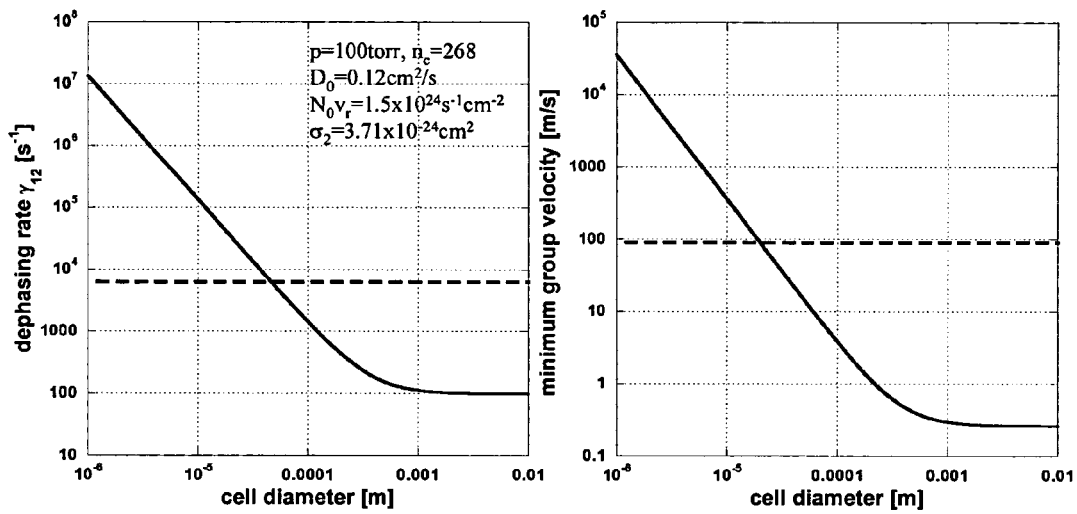

The dependence of the dephasing rates and group velocity on the cell dimensions is shown in FIG. 15(b). The dashed horizontal lines represent the values measured in the bulk experiment. Two regimes are observed. For cell dimensions larger than a few 100 μm, dephasing rates are determined by buffer gas collisions and are size independent. For smaller cells, collisions with the walls lead to increasing dephasing rates and group velocities proportional to the reciprocal area A. However, the group velocity reduction is still sizable (<300 m/s for a 10 μm diameter cell), which demonstrates the potential of integrated EIT cells for light buffering and information storage (M. D. Lukin, "Colloquium: trapping and manipulating photon states in atomic ensembles", Rev. Mod. Phys. 75, 457 (2003)).

Figure 15C:
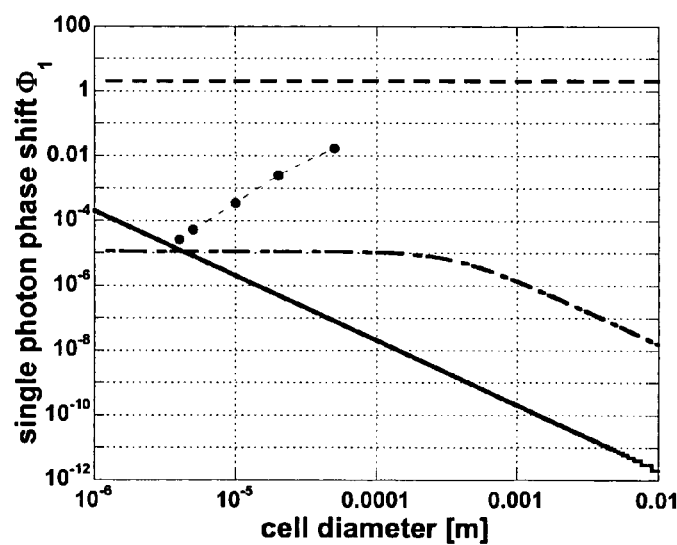

Next, we determine the achievable single photon Kerr phase shift and include the following nonidealities: dispersion (pulse walkoff), absorption due to coherence dephasing, two-photon absorption, and waveguide loss. For all absorption mechanisms, we assume an absorption-length product of $a_i L_i = 0.1$ and calculate the Kerr phase shift for a single photon using $L_i$ in the linear regime for the length dependence described in H. Schmidt and A. Imamoglu, "Giant Kerr nonlinearities using electromagnetically induced transparency", Opt. Lett., 21, 1936, (1996). For the dispersion limit, we determine the maximum phase shift according to the erf-relation given in S. E. Harris, and L. V. Hau, "Nonlinear optics at low light levels", Phys. Rev. Lett., 82, 4611, (1999). We also assume a pulse width of T=1 μs, and a signal detuning from level |4> of $\Delta\omega_{24} = 10\gamma_4$. FIG. 15(c) shows the maximum value of the single-photon phase shift $\Phi_1$ in the presence of the various limiting mechanisms. Several conclusions can be drawn from the graph: The dispersion limited phase shift[9] depends inversely on cell area due to its dependence on the signal intensity. Its value is independent of pulse width and can always be achieved in a cell that is at least as long as the walkoff length. This dependence provides the major motivation for using integrated EIT to obtain large single-photon phase shifts. For example, for a 5 μm cell diameter a phase shift of $10^{-5}$ is feasible, which is six orders of magnitude higher than for a bulk cell and can be measured experimentally. The dephasing-limited curve follows a different behavior and becomes the limiting factor for small cell dimensions. Since the dephasing-induced loss $\alpha_d \sim \gamma_{12}/\Omega_C^2$, it becomes independent of area in the wall-collision limited range. Consequently, the phase shift scales only with signal pulse width as $\Phi_1 \sim 1/T$. One main conclusion is, therefore, that for cell sizes where the phase shift appears dephasing limited, the dispersion limit can be reached by using shorter pulses so that the walkoff length is less than $L_d$. As a result, the dispersion limited curve provides the ultimate limit for cross phase modulation in integrated EIT. An additional loss mechanism not present in conventional bulk cell EIT is waveguide loss. The waveguide loss as a function of core diameter was determined for the ARROW waveguides to be described next and added as circles in FIG. 15(c). It can be seen that the dispersion limit can be reached down to dimensions of about 4 μm. We remark that the waveguide losses shown here are not a fundamental limit as they can be further reduced by improved design. They do, however, limit the possible improvement over the dispersion limit by using group velocity matching (EIT) for the signal pulse as suggested by Lukin and Imamoğlu (M. D. Lukin, and A. Imamoğlu, "Nonlinear optics and quantum entanglement of ultraslow single photons", Phys. Rev. Lett., 84, 1419, (2000)).

Finally, we address the issue of realizing integrated EIT devices with such small cross sections. Optically dense samples are required to achieve the dispersion limit and for hot Rb vapor this requires interaction lengths on the order of 1 mm or longer. Free space optics can therefore not be used to provide small mode areas A over such distances and an integrated waveguide is required. The phase index of the Rb atoms at the EIT resonance is 1 however, precluding conventional index waveguiding. We propose the use of ARROW waveguides with hollow cores for integration of EIT in Rb atoms. The ARROW principle, based on the use of multi-layer claddings that act as a highly reflecting Fabry-Perot etalon for the transverse component of the wave vector, can be used to build ARROW waveguides with core thickness as small as 3.5 μm and up to 1 cm length. FIG. 6(f) presents an SEM image of such a sample and shows the hollow core, the alternating $SiO_2$ and SiN cladding layers and a ridge in the top $SiO_2$ layer for lateral confinement. FIG. 6(g) shows the transmitted mode profile at the output facet. Low-loss single-mode propagation at 785 nm with waveguide loss on the order of 2.1 $cm^{-1}$ was measured, which is sufficiently low for observing large single photon phase shifts. A vapor cell suitable for EIT measurements can be built by filling the waveguides with Rb in a buffer gas atmosphere and by sealing the ends with a transparent polymer followed by a polishing procedure.

In summary, we have presented an analysis for integration of EIT in alkali atoms on a semiconductor chip. We have derived the scaling laws for dephasing rates, achievable group velocity reduction, and single photon Kerr phase shift. Dephasing rates increase at smaller dimensions due to collisions with the walls and limit the group velocity reduction. Single-photon Kerr phase shifts, however, can be increased by several orders of magnitude compared to bulk setups and are fundamentally limited by pulse walkoff (dispersion). We also proposed hollow-core ARROW waveguides as a viable way to build an integrated EIT platform with waveguiding in the low index atomic vapor. This is a promising approach to utilize the power of EIT effects in applications and for the study of the fundamental limits of photon interactions.

Optical Tweezers

Optical tweezers provide a method to hold, direct and manipulate small particles of micron or sub-micron size such as cells or cell parts using light (Ashkin A. History of optical trapping and manipulation of small-neutral particle, atoms, and molecules. [Journal Paper] IEEE Journal of Selected Topics in Quantum Electronics, vol. 6, no.6, November–December 2000, pp. 841–56 and references therein). This has the advantage that no mechanical interaction is present that could damage the specimen. The effect is based on light pressure, i.e., the notion that light carries with it a certain amount of momentum that can be transferred to material objects.

An optical tweezer is generally understood as being a single-beam optical trap as shown in FIG. 16(a) where a laser beam is strongly focused by a high aperture lens. Two types of forces result as the beam hits a small object. One is a scattering force that pushes the object along the direction of the beam, i.e., along x. The second one is the trapping force F, which is directed along-x. If the aperture of the lens is large enough, the trapping force can dominate over the scattering force and trap a particle at a point close to the focus of the lens. No integrated version of such tweezers exists to date. By deliberately shaping (tapering) the lateral profile of an integrated ARROW waveguide with non-solid core (central tapered area in FIG. 16(b), the intensity profile of a Gaussian beam can be emulated. In the same way as in traditional optical tweezers using lenses, the intensity gradient of light propagating along x will induce scattering and trapping forces on a microscopic particle inside the waveguide, leading to an integrated version of optical tweezers. Note that no lenses are required in this case and that the beam profile can be shaped and designed in ways different from profiles obtainable from bulk optics. In a particular application, this concept can be used to hold a particle at the intersection of the ARROW waveguide with another waveguide as shown in FIG. 16(b). This can facilitate optical experiments such as fluorescence studies on the sample particles.

CONCLUSION

While the present invention has been described in connection with several presently preferred or illustrative embodiments, it is to be understood that other similar embodiments may be used or modifications and additions may be made to the described embodiments for performing the same functions of the present invention without deviating therefrom. For example, while exemplary embodiments of the invention are described as including ARROW waveguides, one skilled in the art will recognize that the present invention is not limited thereto, and that the methods described herein may apply to other implementations, and may be applied to any number of such devices and applications without departing from the invention. Therefore, the present invention should not be limited to any single embodiment, but rather should be construed in breadth and scope in accordance with the appended claims.

What is claimed:

1. An optical waveguide, comprising:
a substrate made of a solid material and multiple layers of solid state material disposed on the substrate;
a non-solid core extending through at least one of said multiple layers, whereby said non-solid core may be used to contain a sample material;
a perpendicular waveguide portion for use in injecting light into said non-solid core; and
a sample-injection port in fluid communication with said non-solid core;
wherein said multiple layers of solid state material are constructed to form anti-resonant reflecting layers adjacent to said non-solid core, whereby light is substantially prevented from leaking out of said core in a transverse direction.

2. An optical waveguide as recited in claim 1 wherein said substrate comprises Silicon (Si) and said multiple layers include $SiO_2$ and SiN.

3. An optical waveguide as recited in claim 2 wherein said non-solid core has an index of refraction which is lower than the index of refraction of the surrounding solid-state material, and wherein light can be transmitted with low loss through the non-solid core.

4. An optical waveguide, comprising:
a substrate made of a solid material and multiple layers of solid state material disposed on the substrate;
a non-solid core extending through at least one of said multiple layers, whereby said non-solid core may be used to contain a sample material;
a perpendicular waveguide portion for use in injecting light into said non-solid core; and
a sample-injection port in fluid communication with said non-solid core;
wherein said optical waveguide is generally structured as an anti-resonant reflecting optical waveguide (ARROW).

5. An optical waveguide, comprising:
a substrate made of a solid material and multiple layers of solid state material disposed on the substrate;
a non-solid core extending through at least one of said multiple layers, whereby said non-solid core may be used to contain a sample material;
a perpendicular waveguide portion for use in injecting light into said non-solid core; and
a sample-injection port in fluid communication with said non-solid core;
wherein said substrate comprises Silicon (Si) and said multiple layers include $SiO_2$ and SiN; wherein said non-solid core has an index of refraction which is lower than the index of refraction of the surrounding solid-state material; and wherein said optical waveguide is generally structured as an anti-resonant reflecting optical waveguide (ARROW).

6. An optical waveguide as recited in claim 1 wherein the non-solid core has a substantially square cross-section.

7. An optical waveguide as recited in claim 1 wherein the non-solid core has a substantially rectangular cross-section.

8. An optical waveguide as recited in claim 1 wherein the non-solid core has a substantially semicircular cross-section.

9. An optical waveguide as recited in claim 1, wherein said sample injection port is oriented substantially perpendicularly with respect to a longitudinal axis of said non-solid core.

10. An optical waveguide as recited in claim 1 wherein said substrate comprises a semiconductor material.

11. An optical waveguide as recited in claim 1 wherein said substrate comprises a metal.

12. An optical waveguide as recited in claim 1 wherein said substrate comprises a plastic.

13. An optical waveguide as recited in claim 1 wherein said substrate comprises a polymer.

14. An optical waveguide as recited in claim 1 wherein said substrate comprises a Silicon based glass.

15. An optical waveguide as recited in claim 1 wherein said substrate comprises alumina.

16. An optical waveguide as recited in claim 1 wherein said substrate comprises sapphire.

17. An optical waveguide as recited in claim 1 wherein the layer of solid state material through which said non-solid core extends comprises a material deposited by chemical vapor deposition.

18. An optical waveguide as recited in claim 1 wherein the layer of solid state material through which said non-solid core extends comprises silicon oxy-nitride.

19. An optical waveguide as recited in claim 1 wherein the layer of solid state material through which said non-solid core extends comprises a material sputtered onto said substrate.

20. An optical waveguide as recited in claim 1 wherein the layer of solid state material through which said non-solid core extends comprises a material evaporated onto said substrate.

21. An optical waveguide as recited in claim 1 wherein the layer of solid state material through which said non-solid core extends comprises silicon dioxide.

22. An optical waveguide as recited in claim 1 wherein the layer of solid state material through which said non-solid core extends comprises silicon nitride.

23. An optical waveguide as recited in claim 1 wherein the layer of solid state material through which said non-solid core extends comprises silicon-oxynitride.

24. An optical waveguide as recited in claim 1 wherein the layer of solid state material through which said non-solid core extends comprises a material spun-on said substrate.

25. An optical waveguide as recited in claim 1 wherein the layer of solid state material through which said non-solid core extends comprises a material dip coated onto said substrate.

26. An optical waveguide as recited in claim 1 wherein the waveguide is made using a sacrificial layer material comprising a metal.

27. An optical waveguide as recited in claim 1 wherein the waveguide is made using a sacrificial layer material comprising a polymer.

28. An optical waveguide generally structured as an anti-resonant reflecting optical waveguide (ARROW), comprising:
  a substrate and multiple layers of solid state material, including $SiO_2$ and SiN, disposed on the substrate, and a non-solid core extending through at least one of said multiple layers, wherein said non-solid core has an index of refraction which is lower than the index of refraction of the surrounding solid-state material, and wherein light can be transmitted with low loss through the non-solid core;
  a Fabry-Perot reflector adjacent to said non-solid core, for substantially preventing light from leaking out of said core in a transverse direction;
  a perpendicular waveguide portion for use in injecting light into said non-solid core for measuring fluorescence characteristics associated with the sample material; and
  a sample-injection port for injecting a fluid into said non-solid core, said sample injection port being oriented substantially perpendicularly with respect to a longitudinal axis of said non-solid core;
  whereby said non-solid core may be used to contain a sample material whose light transmission, absorption, and/or interference characteristics are to be measured.

29. An optical waveguide as recited in claim 28 wherein the non-solid core has a substantially square cross-section.

30. An optical waveguide as recited in claim 28 wherein the non-solid core has a substantially rectangular cross-section.

31. An optical waveguide as recited in claim 28 wherein the non-solid core has a substantially semicircular cross-section.

32. An optical waveguide as recited in claim 1, comprising a sample material comprising an alkali vapor in said non-solid core.

33. An optical waveguide as recited in claim 1, comprising a sample material comprising rubidium in said non-solid core.

34. An optical waveguide as recited in claim 28, comprising a sample material comprising an alkali vapor in said non-solid core.

35. An optical waveguide as recited in claim 28, comprising a sample material comprising rubidium in said non-solid core.

* * * * *